United States Patent [19]
Suzuki et al.

[11] Patent Number: 5,670,498
[45] Date of Patent: Sep. 23, 1997

[54] 8-SUBSTITUTED STYRYL XANTHINE DERIVATIVES

[75] Inventors: Fumio Suzuki, Mishima; Junichi Shimada; Nobuaki Koike, both of Shizuoka-ken; Hiroshi Kase, Koganei; Joji Nakamura, Shizuoka-ken; Shizuo Shiozaki, Fuji; Hiromi Nonaka, Shizuoka-ken, all of Japan

[73] Assignee: Kyowa Hakko Kogyo Co., Ltd., Tokyo, Japan

[21] Appl. No.: 527,497

[22] Filed: Sep. 13, 1995

Related U.S. Application Data

[63] Continuation of Ser. No. 171,602, Dec. 22, 1993, abandoned.

[30] Foreign Application Priority Data

Dec. 24, 1992 [JP] Japan .................. 4-344116

[51] Int. Cl.⁶ .................. C07D 473/12; C07D 473/10; C07D 473/06; A61K 31/52
[52] U.S. Cl. .................. 514/212; 514/234.2; 514/263; 540/575; 540/600; 544/118; 544/267; 544/271; 544/272
[58] Field of Search .................. 514/263, 212, 514/234.2; 544/267, 271, 272, 118; 540/575, 600

[56] References Cited

U.S. PATENT DOCUMENTS 5,270,316  12/1993  Suzuki .................. 544/251

FOREIGN PATENT DOCUMENTS 0092398  10/1983  European Pat. Off. .
0203721  12/1986  European Pat. Off. .

OTHER PUBLICATIONS

Papa, Eur. J. Pharmacology 232, 247 (1993).
Maj et al, J Neural Trans. 52, 189(1981).
Ossowska, Eur. J. Pharm. 182, 327 (1990).
"Pharm Basis of Therapeutics", 8th Edition (1990) pp. 406–407, 470–471.
Principles of Internal Medicine, vol. 2 (1991) p. 2060.
Jacobsen, J Med Chem 35, 407(1992).
Abstract for Larsen *Tidsskrift for Den Narske Laege Forening* 115(10) 1236–9 (1995).
Kaupp et al., Chem. Ber., vol. 119 (1986) 1525:39.
Erickson et al., J. Med. Chem., vol. 34, No. 4 (1991) 1431:35.
LU Govkin et al Chemical Abstracts, vol. 60, No. 38 (1964) 1741h.

Primary Examiner—Mark L. Berch
Attorney, Agent, or Firm—Fitzpatrick, Cella, Harper & Scinto

[57] ABSTRACT

Disclosed are xanthine derivatives represented by the following Formula (I):

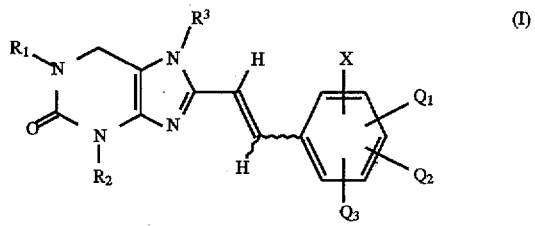

in which $R^1$, $R^2$, and $R^3$ independently represent hydrogen or lower alkyl;

$Q^1$, $Q^2$, and $Q^3$ independently represent hydrogen, lower alkyl, lower alkoxy, or halogen;

and X represents —$COR^4$ (in which $R^4$ represents hydrogen, hydroxy, lower alkyl, or lower alkoxy) or —$SO_2R_5$ {in which $R^5$ represents hydroxy, lower alkoxy, trifluoromethyl,

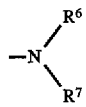

in which $R^6$ and $R^7$ independently represent hydrogen, hydroxy-substituted or unsubstituted lower alkyl, aryl, or

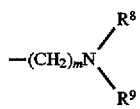

(in which m represents an integer of 1 to 3; and $R^8$ and $R^9$ independently represent hydrogen or lower alkyl), or

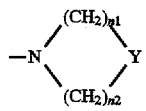

(in which Y represents a single bond, oxygen, or N—$R^{10}$ in which $R^{10}$ represents hydrogen or lower alkyl; and n1 and n2 independently represent an integer of 1 to 3)}, and pharmaceutically acceptable salts thereof.

10 Claims, No Drawings

8-SUBSTITUTED STYRYL XANTHINE DERIVATIVES

This application is a continuation of application Ser. No. 08/171,602, filed Dec. 22, 1993, now abandoned.

BACKGROUND OF THE INVENTION

The present invention relates to novel 8-substituted xanthine derivatives and pharmaceutically acceptable salts thereof which are expected to exhibit therapeutic effects on various kinds of diseases caused by hyperergasia of adenosine $A_2$ receptors, for example, Parkinson's disease, senile dementia, depression, asthma, and osteoporosis.

It is known that adenosine exhibits neurotransmitter depressing activity, bronchospasmic activity, bone absorption promoting activity, and the like via an $A_2$ receptor. Therefore, adenosine $A_2$ receptor antagonists (hereinafter referred to as $A_2$-antagonists) are expected as therapeutic agents for various kinds of diseases caused by hyperergasia of adenosine $A_2$ receptors, for example, therapeutic agents for Parkinson's disease, anti-dementia agents, antidepressants, anti-asthmatic agents, and therapeutic agents for osteoporosis.

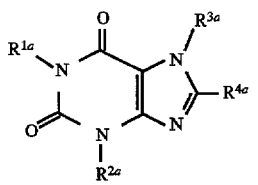

(A)

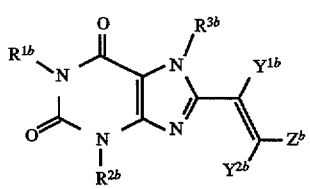

(B)

It is known that adenosine antagonistic activity is found in compounds represented by Formula (A) in which $R^{1a}$ and $R^{2a}$ independently represent methyl or propyl, $R^{3a}$ represents hydrogen, and $R^{4a}$ represents substituted or unsubstituted phenyl, aromatic heterocyclic group, cycloalkyl, styryl, or phenylethyl [J. Med. Chem., 34, 1431 (1991)]. Further, U.S. Pat. No. 3,641,010 discloses, as cerebral stimulants, compounds represented by Formula (B) in which $R^{1b}$ and $R^{2b}$ independently represent methyl or ethyl, $R^{3b}$ represents methyl, $Y^{1b}$ and $Y^{2b}$ represent hydrogen, and $Z^b$ represents phenyl or 3,4,5-trimethoxyphenyl. WO92/06976 discloses, as compounds having an adenosine $A_2$ receptor antagonistic activity and therapeutic effects on asthma and osteoporosis, compounds represented by Formula (B) in which $R^{1b}$ and $R^{2b}$ independently represent hydrogen, propyl, butyl, or allyl, $R^{3b}$ represents hydrogen or lower alkyl, $Y^{1b}$ and $Y^{2b}$ independently represent hydrogen or methyl, and $Z^b$ represents substituted or unsubstituted phenyl, pyridyl, imidazolyl, furyl, or thienyl. Furthermore, other compounds represented by Formula (B) are known. One is 8-styryl caffeine which is a compound of Formula (B) in which $R^{1b}$, $R^{2b}$, and $R^{3b}$ represent methyl, $Y^{1b}$ and $Y^{2b}$ represent hydrogen, and $Z^b$ represents phenyl [Chem. Ber. 119, 1525 (1986)]. Another is a compound of Formula (B) in which $R^{1b}$, $R^{2b}$, and $R^{3b}$ represent methyl, $Y^{1b}$ and $Y^{2b}$ represent hydrogen, and $Z^b$ represents pyridyl, quinolyl, or methoxy-substituted or unsubstituted benzothiazolyl [Chem. Abst. 60, 1741h (1964)]. However, there is no description with regard to the pharmacological activity of any of these compounds.

SUMMARY OF THE INVENTION

An object of the present invention is to provide novel 8-substituted xanthine derivatives and pharmaceutically acceptable salts thereof which are expected to exhibit therapeutic effects on various kinds of diseases caused by hyperergasia of adenosine $A_2$ receptors, for example, Parkinson's disease, senile dementia, depression, asthma, and osteoporosis.

The present invention relates to xanthine derivatives represented by the following Formula (I):

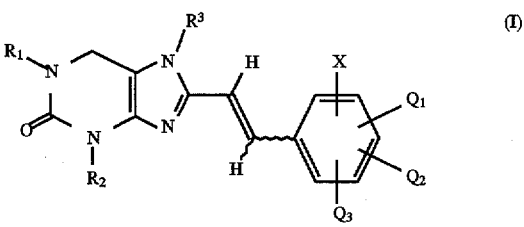

(I)

in which $R^1$, $R^2$, and $R^3$ independently represent hydrogen or lower alkyl;

$Q^1$, $Q^2$, and $Q^3$ independently represent hydrogen, lower alkyl, lower alkoxy, or halogen;

and X represents —$COR^4$ (in which $R^4$ represents hydrogen, hydroxy, lower alkyl, or lower alkoxy) or —$SO_2R^5$ {in which $R^5$ represents hydroxy, lower alkoxy, trifluoromethyl,

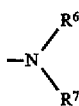

in which $R^6$ and $R^7$ independently represent hydrogen, hydroxy-substituted or unsubstituted lower alkyl, aryl, or

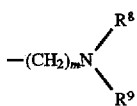

(in which m represents an integer of 1 to 3; and $R^8$ and $R^9$ independently represent hydrogen or lower alkyl), or

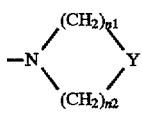

(in which Y represents a single bond, oxygen, or N—$R^{10}$ in which $R^{10}$ represents hydrogen or lower alkyl; and n1 and n2 independently represent an integer of 1 to 3)}, and pharmaceutically acceptable salts thereof.

The compounds represented by Formula (I) are hereinafter referred to as Compounds (I), and the same applies to compounds of other formula numbers.

DETAILED DESCRIPTION OF THE INVENTION

In the definitions of the groups in Formula (I), the lower alkyl means a straight-chain or branched alkyl group having 1 to 6 carbon atoms, such as methyl, ethyl, propyl, isopropyl, butyl, isobutyl, sec-butyl, tert-butyl, pentyl, neopentyl, and hexyl, and the aryl means phenyl or naphthyl. The lower alkyl moiety of the lower alkoxy has the same meaning as the lower alkyl defined above. The halogen means fluorine, chlorine, bromine, and iodine.

The above-mentioned pharmaceutically acceptable salts of Compounds (I) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The processes for producing Compounds (I) are described below.

Process 1

Compound (Ia) [Compound (I) in which X is $SO_3H$] can be prepared by the following reaction step:

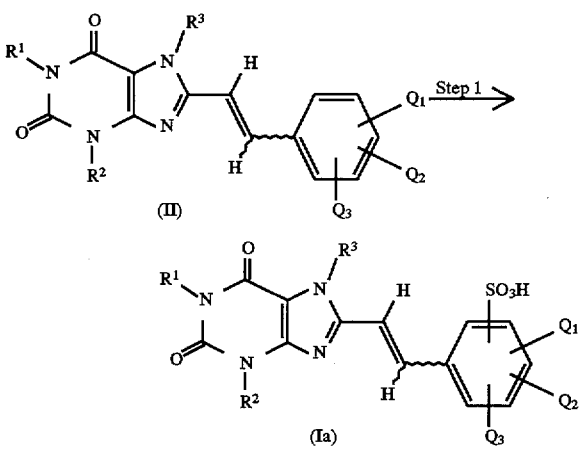

(In the formulae, $R^1$, $R^2$, $R^3$, $Q^1$, $Q^2$, and $Q^3$ have the same meanings as defined above.)

(STEP 1)

Compound (Ia) can be obtained by sulfonylating a xanthine derivative (II) obtained by a known method (WO92/06976) or a method similar thereto, usually in a solvent.

Examples of the sulfonylating agent are chlorosulfonic acid, sulfuric acid, sulfur trioxide, sulfur trioxide pyridine complex, sodium sulfite, and sulfuryl chloride. Examples of the solvent are halogenated hydrocarbons such as carbon tetrachloride, chloroform, and ethylene dichloride, thionyl chloride, nitromethane, and dimethylformamide. When sulfuric acid is used as the sulfonylating agent, no solvent is employed. The reaction is carried out at −40° to 70° C. and is completed in 30 minutes to 3 hours.

Process 2

Compound (Ib) [Compound (I) in which X is $SO_2R^{5a}$ (wherein $R^{5a}$ represents groups other than hydroxy and trifluoromethyl in the definition of $R^5$)] can be prepared by the following reaction steps.

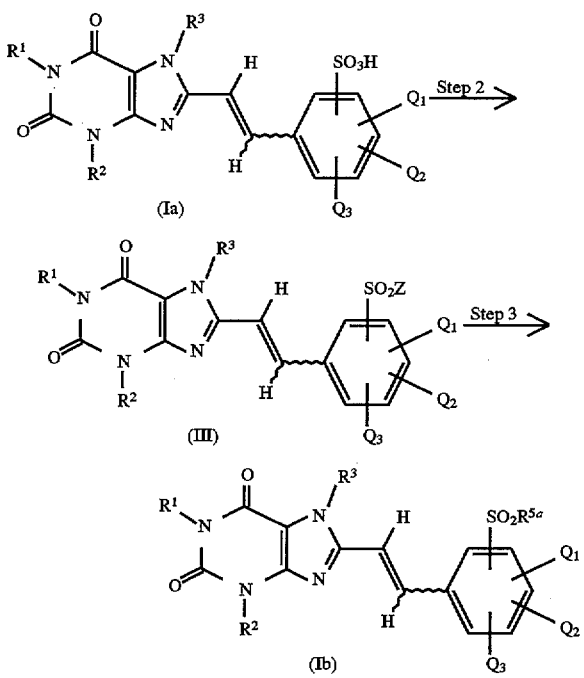

(In the formulae, $R^1$, $R^2$, $R^3$, $R^{5a}$, $Q^1$, $Q^2$, and $Q^3$ have the same meanings as defined above; and Z represents chlorine, bromine, or iodine.)

(STEP 2)

Compound (III) can be obtained by reaction of Compound (Ia) obtained in Process 1 or a sodium salt thereof with a halogenating agent in a solvent.

Examples of the halogenating agent are oxyhalogenated phosphine such as phosphorus oxychloride and phosphorus oxybromide, pentahalogenated phosphine such as phosphorus pentachloride, halogenated sulfonic acid such as chlorosulfonic acid, and dihalogenated sulfoxide such as thionyl chloride. Examples of the solvent are halogenated hydrocarbons such as carbon tetrachloride, chloroform, and ethylene dichloride, ethers such as dioxane and tetrahydrofuran, and dimethylformamide. When excess halogenating agent is used, the reaction may be carried out without a solvent. The reaction is carried out at −20° to 200° C. and is completed in 0.5 to 24 hours.

(STEP 3)

Compound (Ib) can be obtained by reaction of Compound (III) with a corresponding amine or alcohol in a solvent in the presence of a base. Compound (III) obtained in STEP 2 may be formed in the reaction system and then used without being isolated.

Examples of the base are pyridine, 2,6-lutidine, triethylamine, 4-dimethylaminopyridine, and N-methylmorpholine. The solvent may be selected appropriately from those described in STEP 1. The reaction is carried out at −80° to 50° C. and is completed in 0.5 to 24 hours.

Process 3

Compound (Ic) [Compound (I) in which X is $COR^{4a}$ (wherein $R^{4a}$ represents lower alkoxy in the definition of $R^4$)] and Compound (Id) [Compound (I) in which X is COOH] can be prepared by the following reaction steps.

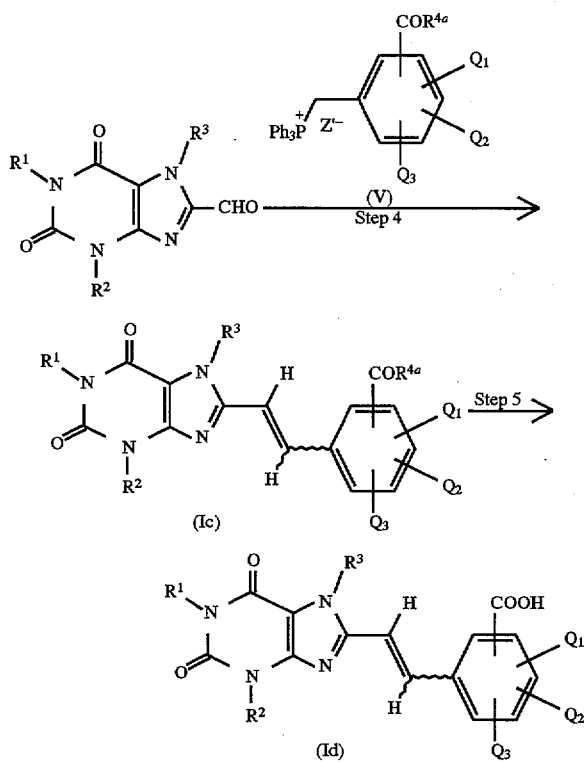

(In the formulae, $R^1$, $R^2$, $R^3$, $R^{4a}$, $Q^1$, $Q^2$, and $Q^3$ have the same meanings as defined above; Z' represents chlorine, bromine, or iodine; and Ph represents phenyl.)

(STEP 4)

Compound (Ic) can be obtained by reaction of Compound (IV) obtained by a known method [Chem. Ber., 95, 414 (1962)] with a phosphonium salt (V) in a solvent in the presence of a base.

Examples of the base are alkali metal carbonates such as sodium carbonate and potassium carbonate, alkali metal hydrides such as sodium hydride and potassium hydride, alkyl lithiums such as butyl lithium, and alkali metal alkoxides such as potassium tert-butoxide and potassium tert-amyl alcoholate. Examples of the solvent are aromatic hydrocarbons such as toluene and xylene, ethers such as dioxane and tetrahydrofuran, dimethylformamide, and dimethylsulfoxide. The reaction is carried out at 0° to 120° C. and is completed in 0.5 to 24 hours.

(STEP 5)

Compound (Id) can be obtained by hydrolysis of an ester group of Compound (Ic) in a solvent in the presence of a suitable additive.

Examples of the additive are alkali metal hydroxides such as lithium hydroxide, sodium hydroxide, and potassium hydroxide, alkaline earth metal hydroxides such as calcium hydroxide and barium hydroxide, halogenated lithiums such as lithium chloride, and alkali metal alkoxides such as potassium tert-butoxide. As the solvent, alcohols such as methanol and ethanol, ethers such as dioxane and tetrahydrofuran, dimethylformamide, dimethylsulfoxide, pyridine, and, if necessary, water or the like may be used in combination. The reaction is carried out at 0° to 120° C. and is completed in 0.5 to 24 hours.

Process 4

Compound (Iea) [Compound (I) in which X is $COCH_3$], and Compound (Id) can be prepared by the following reaction steps.

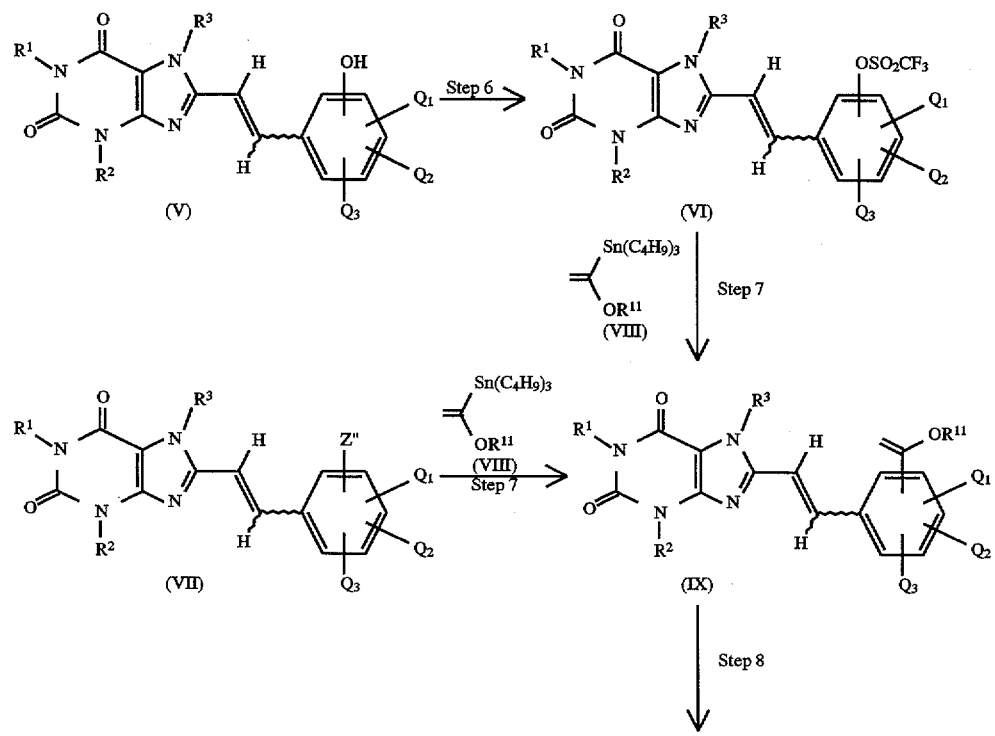

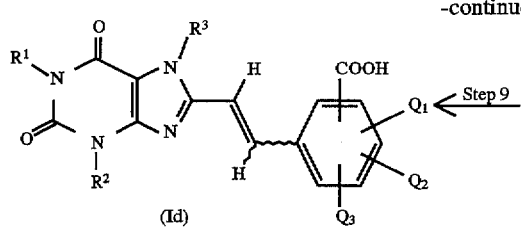
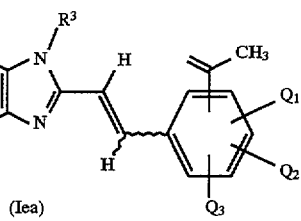

(In the formulae, $R^1$, $R^2$, $R^3$, $Q^1$, $Q^2$, and $Q^3$ have the same meanings as defined above; $R^{11}$ represents lower alkyl; and Z" represents bromine or iodine.)

The lower alkyl in the definition of $R^{11}$ has the same meaning as defined above.

(STEP 6)

Compound (VI) can be obtained by reaction of Compound (V) obtained by a known method (EP-A-0565377) or a method similar thereto with trifluoromethanesulfonic anhydride, trifluoromethanesulfonyl chloride, or N-phenyl-N-(trifluoromethanesulfonyl)trifluoromethanesulfonamide in a solvent in the presence of a base.

Examples of the base are organic amines such as triethylamine, diisopropylethylamine, 4-dimethylaminopyridine, and pyridine, and inorganic carbonates such as potassium carbonate. Examples of the solvent are halogenated hydrocarbons such as methylene chloride and ethylene dichloride. The reaction is carried out at −30° to 100° C. and is completed in 0.5 to 10 hours.

(STEP 7)

Compound (IX) can be obtained by reaction of Compound (VI) or Compound (VII) obtained by a known method (EP-A-0565377) or a method similar thereto with a tin compound (VIII) in a solvent in the presence of a transition metal catalyst.

Examples of the transition metal catalyst are palladium catalysts such as dichlorobis(triphenylphosphine)palladium and palladium acetate. An example of the tin compound (VIII) is (1-ethoxyvinyl)tributyltin. Examples of the solvent are aromatic hydrocarbons such as toluene and xylene, ethers such as dioxane and tetrahydrofuran, dimethylformamide, and dimethylsulfoxide. Lithium chloride may be added, if necessary. The reaction is carried out at 0° to 120° C. and is completed in 0.5 to 24 hours.

(STEP 8)

Compound (Iea) can be obtained by hydrolysis of a vinyl ether group of Compound (IX) in a solvent in the presence of a suitable acid.

Examples of the acid are protic acids such as hydrochloric acid and p-toluenesulfonic acid. As the solvent, alcohols such as methanol and ethanol, ethers such as dioxane and tetrahydrofuran, ketones such as acetone and 2-butanone, dimethylformamide, dimethylsulfoxide, pyridine, water, and the like may be used solely, or if necessary in combination. The reaction is carried out at 0° to 120° C. and is completed in 0.5 to 24 hours.

(STEP 9)

Compound (Id) can be obtained by subjecting Compound (Iea) to a haloform reaction in a solvent in the presence of a base.

Examples of the base are alkali metal hydroxides such as sodium hydroxide and potassium hydroxide. Examples of the halogen used in the haloform reaction are bromine and iodine. As the solvent, alcohols such as methanol and ethanol, ethers such as dioxane and tetrahydrofuran, dimethylformamide, water, and the like may be used solely, or if necessary in combination. The reaction is carried out at 0° to 120° C. and is completed in 0.5 to 24 hours.

Process 5

Compound (Ie) [Compound (I) in which X is $COR^{4b}$ (wherein $R^{4b}$ represents hydrogen or lower alkyl in the definition of $R^4$)] can be prepared by the following reaction step.

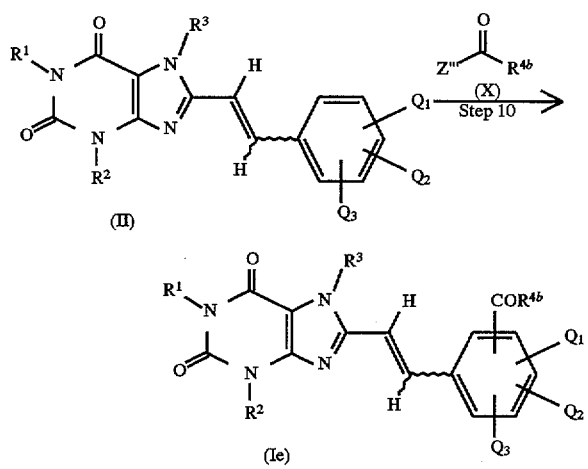

(In the formulae, $R^1$, $R^2$, $R^3$, $R^{4b}$, $Q^1$, $Q^2$, and $Q^3$ have the same meanings as defined above; and Z''' represents chlorine, bromine, or iodine.)

(STEP 10)

Compound (Ie) can be obtained by reaction of Compound (II) with an equivalent amount of Compound (X) in a solvent in the presence of a Lewis acid.

As the Lewis acid, 1–3 equivalents, preferably 2 equivalents of aluminum chloride, or the like is used. Examples of the solvent are halogenated hydrocarbons such as dichloromethane and dichloroethane. The reaction is carried out at 0° C. to room temperature and is completed in 1 to 24 hours.

The desired compounds in the processes described above can be isolated and purified by purification methods conventionally used in organic synthetic chemistry, for example, filtration, extraction, washing, drying, concentration, recrystallization, and various kinds of chromatography.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or a base to form a salt.

Compounds (I) can exist in the form of geometrical isomers such as an (E)-isomer and a (Z)-isomer, and the present invention covers all possible isomers including these geometrical isomers and mixtures thereof. In the case where separation between an (E)-isomer and a (Z)-isomer is desired, they can be isolated and purified by fractionation methods, for example, fractional crystallization, fractional precipitation, and fractional dissolution.

Compounds (I) and pharmaceutically acceptable salts thereof may be in the form of adducts with water or various solvents, which are also within the scope of the present invention.

Examples of Compounds (I) are shown in Table 1.

TABLE 1

| Compound No. (Example No.) | $R^1$ | $R^2$ | Q3 |
|---|---|---|---|
| 1(1) | $CH_3(CH_2)_2$ | $CH_3(CH_2)_2$ | 4-OCH₃, 3-OCH₃, 5-SO₃H phenyl |
| 2(2) | $CH_3(CH_2)_2$ | $CH_3(CH_2)_2$ | 4-OCH₃, 3-OCH₃, 5-SO₂N(CH₂CH₃)₂ phenyl |
| 3(3) | $CH_3(CH_2)_2$ | $CH_3(CH_2)_2$ | 4-OCH₃, 3-OCH₃, 5-SO₂N[(CH₂)₂CH₃]₂ phenyl |

TABLE 1-continued

| Compound No. (Example No.) | $R^1$ | $R^2$ | Q3 |
|---|---|---|---|
| 4(4) | $CH_3(CH_2)_2$ | $CH_3(CH_2)_2$ | 4-OCH₃, 3-OCH₃, 5-SO₂-piperidinyl phenyl |
| 5(5) | $CH_3(CH_2)_2$ | $CH_3(CH_2)_2$ | 4-OCH₃, 3-OCH₃, 5-SO₂-(4-methylpiperazinyl) phenyl |
| 6(6) | $CH_3(CH_2)_2$ | $CH_3(CH_2)_2$ | 4-OCH₃, 3-OCH₃, 5-SO₂N(CH₃)(CH₂)₂N(CH₃)₂ phenyl |
| 7(7) | $CH_3(CH_2)_2$ | $CH_3(CH_2)_2$ | 4-CO₂CH₃ phenyl |
| 8(7)* | $CH_3(CH_2)_2$ | $CH_3(CH_2)_2$ | 4-CO₂CH₃ phenyl |

TABLE 1-continued

[Structure: xanthine with N-R¹, N-R², N-CH₃, linked via vinyl to substituted phenyl ring with X, Q₁, Q₂, Q₃]

| Compound No. (Example No.) | R¹ | R² | Q₃ (substituent pattern) |
|---|---|---|---|
| 9(8) | CH₃(CH₂)₂ | CH₃(CH₂)₂ | phenyl with OCH₃, OCH₃, SO₂NH₂ |
| 10(9) | CH₃(CH₂)₂ | CH₃(CH₂)₂ | phenyl with OCH₃, OCH₃, SO₂NH-phenyl |
| 11(10) | CH₃(CH₂)₂ | CH₃(CH₂)₂ | phenyl with OCH₃, OCH₃, OCH₃, SO₃H |
| 12(11) | CH₃(CH₂)₂ | CH₃(CH₂)₂ | phenyl with OCH₃, OCH₃, OCH₃, SO₂NH₂ |
| 13(12) | CH₃(CH₂)₂ | CH₃(CH₂)₂ | phenyl with OCH₃, OCH₃, OCH₃, O₂S-N(CH₃)(CH₂)₂N(CH₃)₂ |
| 14(13) | CH₃(CH₂)₂ | CH₃(CH₂)₂ | phenyl with OCH₃, OCH₃, SO₂NH(CH₂)₂OH |
| 15(14) | CH₃(CH₂)₂ | CH₃(CH₂)₂ | phenyl with CH₃, CH₃, SO₃H |
| 16(15) | CH₃CH₂ | CH₃CH₂ | phenyl with OCH₃, SO₃H |
| 17(16) | CH₃CH₂ | CH₃CH₂ | phenyl with OCH₃, SO₂NH₂ |
| 18(17)* | CH₃(CH₂)₂ | CH₃(CH₂)₂ | phenyl with CO₂H |
| 19(18) | CH₃(CH₂)₂ | CH₃(CH₂)₂ | phenyl with CO₂H |
| 20(19) | CH₃CH₂ | CH₃CH₂ | phenyl with OCH₃, CO₂CH₃ |
| 21(20) | CH₃(CH₂)₂ | CH₃(CH₂)₂ | phenyl with OCH₃, CO₂CH₃ |
| 22(21) | CH₃CH₂ | CH₃CH₂ | phenyl with OCH₃, CO₂H |

TABLE 1-continued

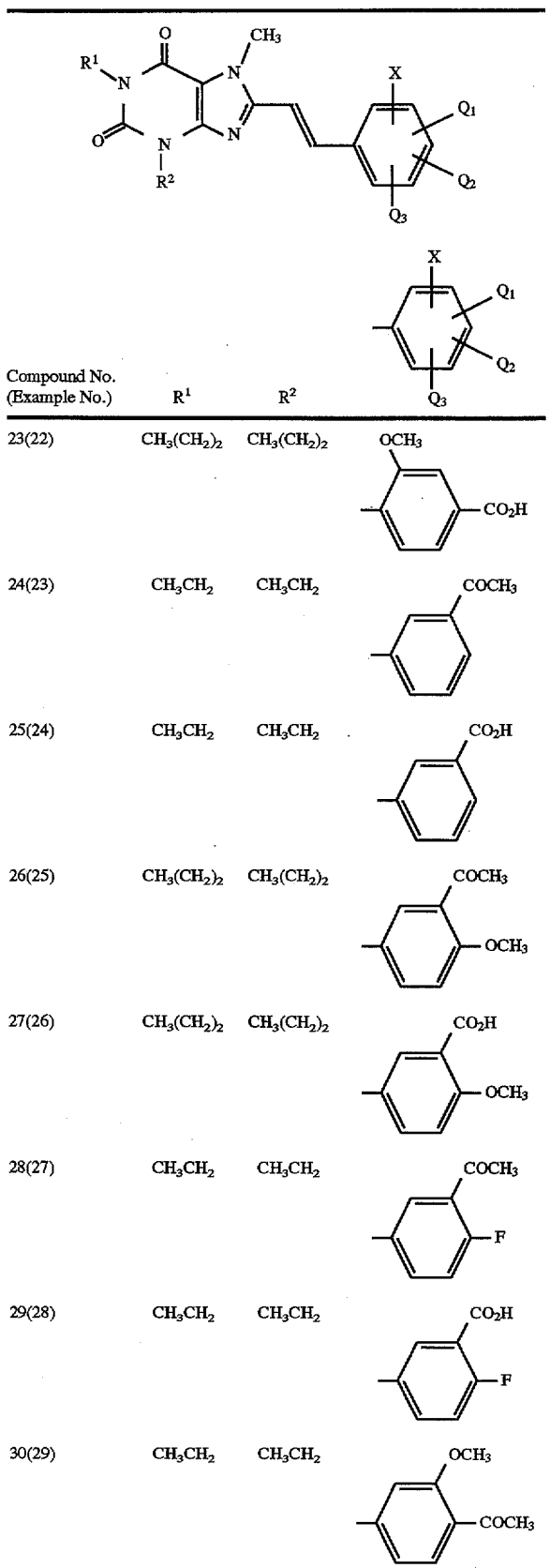

| Compound No. (Example No.) | R¹ | R² | |
|---|---|---|---|
| 23(22) | $CH_3(CH_2)_2$ | $CH_3(CH_2)_2$ | 3-OCH₃, 4-CO₂H phenyl |
| 24(23) | $CH_3CH_2$ | $CH_3CH_2$ | 3-COCH₃ phenyl |
| 25(24) | $CH_3CH_2$ | $CH_3CH_2$ | 3-CO₂H phenyl |
| 26(25) | $CH_3(CH_2)_2$ | $CH_3(CH_2)_2$ | 2-COCH₃, 3-OCH₃ phenyl |
| 27(26) | $CH_3(CH_2)_2$ | $CH_3(CH_2)_2$ | 2-CO₂H, 3-OCH₃ phenyl |
| 28(27) | $CH_3CH_2$ | $CH_3CH_2$ | 2-COCH₃, 3-F phenyl |
| 29(28) | $CH_3CH_2$ | $CH_3CH_2$ | 2-CO₂H, 3-F phenyl |
| 30(29) | $CH_3CH_2$ | $CH_3CH_2$ | 2-OCH₃, 3-COCH₃ phenyl |

TABLE 1-continued

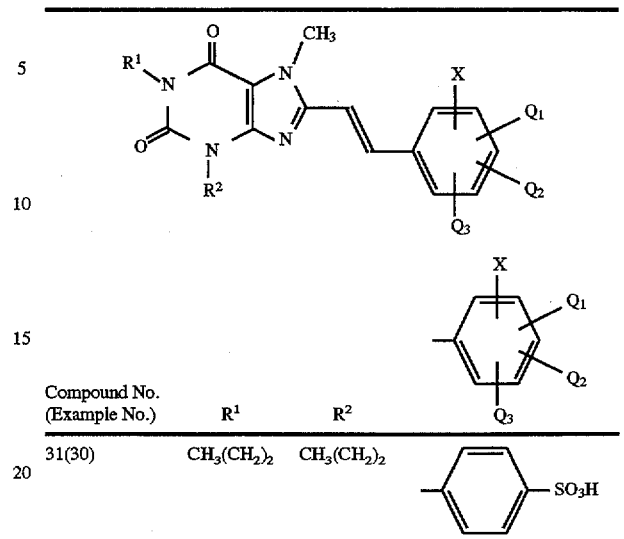

| Compound No. (Example No.) | R¹ | R² | |
|---|---|---|---|
| 31(30) | $CH_3(CH_2)_2$ | $CH_3(CH_2)_2$ | 4-SO₃H phenyl |

*Z form

The pharmacological activities of Compounds (I) are shown below by test examples.

Test Example 1

Acute Toxicity Test

Test compounds were orally administered to groups of dd-strain male mice weighing 20±1 g, each group consisting of three mice (po; 300 mg/kg). Seven days after the administration, minimum lethal dose (MLD) of each compound was determined by observing the mortality.

The results on Compounds (I) are shown in Table 2. As shown in Table 2, the toxicity of Compounds (I) is weak. Therefore, these compounds can be safely used in a wide range of doses.

TABLE 2

| Compound | MLD (mg/kg) |
|---|---|
| 1 | >300 |
| 8 | >300 |
| 15 | >300 |
| 18 | >300 |

Test Example 2

Adenosine Receptor Antagonistic Activity (Adenosine $A_2$ Receptor Binding Test)

The test was conducted according to the method of Bruns et al. [Mol. Pharmacol., 29, 331 (1986)] with slight modification.

Corpus striatum of a rat was suspended in ice-cooled 50 mM Tris hydroxymethyl aminomethane hydrochloride (Tris HCl) buffer (pH 7.7) by using Polytron homogenizer (manufactured by Kinematicas Co.). The suspension was centrifuged (50,000×g, 10 minutes), and the precipitate was suspended again in the same amount of 50 mM Tris HCl buffer. The suspension was centrifuged under the same conditions, and the final precipitate was suspended once again in 50 mM Tris HCl buffer containing 10 mM magnesium chloride and 0.02 unit/mg tissue of adenosine deaminase (manufactured by Sigma Co.) to give a tissue concentration of 5 mg (wet weight)/ml.

To 1 ml of the tissue suspension thus prepared were added 50 μl of a mixture of N-ethylcarboxamidoadenosine labeled with tritium ($^3$H-NECA: 26 Ci/mmol, manufactured by Amersham Co.) (final concentration: 3.8 nM) and cyclopentyladenosine (CPA, manufactured by Sigma Co.) (final concentration: 50 nM), and 50 μl of a test compound. The resulting mixture was allowed to stand at 25° C. for 120 minutes and then rapidly filtered by suction through a glass fiber filter (GF/C, manufactured by Whatman Co.). The filter was immediately washed three times with 5 ml each of ice-cooled 50 mM Tris HCl buffer, and transferred to a vial, and a scintillator (EX-H by Wako Pure Chemical Industries, Ltd.) was added thereto. The radioactivity on the filter was determined with a liquid scintillation counter (manufactured by Packard instrument Co.).

The inhibition rate of the test compound against the binding of $A_2$ receptors ($^3$H-NECA binding) was calculated by the following equation:

$$\text{Inhibition Rate (\%)} = \left(1 - \frac{[B] - [N]}{[T] - [N]}\right) \times 100$$

[Notes]
1. "*B*" means the amount of radioactivity of $^3$H-NECA bound in the presence of a test compound at a concentration shown in Table 3.
2. "*T*" means the amount of radioactivity of $^3$H-NECA bound in the absence of a test compound
3. "*N*" means the amount of radioactivity of $^3$H-NECA bound in the presence of 100 μM CPA.

The similar procedure as above was repeated to determine the radioactivity bound to the $A_2$ receptors using 50 μl of CGS 21680 labeled with tritium {$^3$H-2-[p-(2-carboxyethyl)phenethylamino]-5'-(N-ethylcarboxamide)adenosine: 40 Ci/mmol, manufactured by New England Nuclear Co. [J. Pharmacol. Exp. Ther., 251, 888 (1989)]} (final concentration: 4.0 nM) in place of 50 μl of the mixture of N-ethylcarboxamidoadenosine labeled with tritium ($^3$H-NECA: 26 Ci/mmol, manufactured by Amersham Co.) (final concentration: 3.8 nM) and cyclopentyladenosine (CPA, manufactured by Sigma Co.) (final concentration: 50 nM).

The inhibition rate of the test compound against the binding of $A_2$ receptors ($^3$H-CGS 21680 binding) was calculated by the following equation:

$$\text{Inhibition Rate (\%)} = \left(1 - \frac{[B] - [N]}{[T] - [N]}\right) \times 100$$

[Notes]
1. "*B*" means the amount of radioactivity of []$^3$H-CGS 21689 bound in the presence of a test compound at a concentration shown in Table 3.
2. "*T*" means the amount of radioactivity of $^3$H-CGS21680 bound in the absence of a test compound.
3. "*N*" means the amount of radioactivity of $^3$H-CGS 21680 bound in the presence of 100 μM CPA.

The results are shown in Table 3. The Ki values shown in the table were calculated by the following equation:

$$Ko = \frac{IC_{50}}{1 + \frac{L}{Kd} + \frac{C}{Kc}}$$

[Notes]
$IC_{50}$: Concentration at2which the inhibition rate is 50%
L: Concentratiion of $^3$H-NECA or $^3$H-CGS 21680
Kd: Dissociation constant of $^3$H-NECA or $^3$H-CGS 21680
C: Concentration of CPA
Kc: Inhibition constant of CPA

TABLE 3

| Compd. | $A_2$ Receptor Inhibition Rate (%) | | | | $K_i$ (nM) |
|---|---|---|---|---|---|
| | $10^{-7}$M | $10^{-6}$M | $10^{-5}$M | $10^{-4}$M | |
| 1 | | | 80 | 95 | 670 |
| 2 | | | 97 | 112 | |
| 3 | | | 92 | 91 | |
| 4 | | | 74 | 60 | |
| 7 | | | 77 | 92 | |
| 8 | | | 92 | 101 | |
| 11 | | | 93 | 93 | |
| 12 | | | 68 | 76 | |
| 13 | | | 69 | 89 | |
| 18 | | 72 | | | |
| 19 | 68 | 94 | | | |
| 20 | 69* | 88* | | | |
| 21 | 80* | 94* | | | |
| 22 | 60* | 92* | | | |
| 23 | 70* | 95* | | | |
| 24 | 85* | 99* | | | 13 |
| 26 | 66* | 93* | | | |
| 28 | 76* | 86* | | | |
| 30 | 83* | 95* | | | |
| 31 | 56* | 89* | | | |

*; [$^3$H]CGS 21680 was used.

Compounds (I) and pharmaceutically acceptable salts thereof exhibit a potent adenosine $A_2$ receptor antagonistic activity. Thus, they are effective against various kinds of diseases caused by hyperergasia of adenosine $A_2$ receptors, for example, Parkinson's disease, senile dementia, depression, asthma, and osteoporosis.

Test Example 3

Effect on Haloperidol-Induced Catalepsy

Parkinson's disease is a clinical syndrome caused by degeneration of nigrostriatal dopaminergic neurons. Systemic administration of haloperidol (dopamine $D_1/D_2$ antagonist) induces catalepsy resulting from the blockade of postsynaptic dopamine $D_2$ receptors. It is generally accepted that this haloperidol-induced catalepsy is a classical model of parkinsonism in humans [Eur. J. Pharmacol., 182, 327 (1990)].

The experiment was performed by using several groups of 5-weeks-old male ddY mice (weighing 22 to 24 g, Japan SLC), each group consisting of 5 mice. Haloperidol (Janssen Pharmaceutica) suspended in 0.3% CMC was intraperitoneally administered to each mouse at a dose of 1.0 mg/kg. Test compounds were suspended in injectable distilled water (Otsuka Pharmaceutical Co., Ltd.) containing Tween 80 [polyoxyethylene (20) sorbitan monooleate]. L-DOPA (Kyowa Hakko Kogyo Co., Ltd.) and benserazide hydrochloride (Kyowa Hakko Kogyo Co., Ltd.) were suspended in 0.3% CMC. One hour after the haloperidol administration, the test compound suspensions and the control suspension [injectable distilled water (Otsuka Pharmaceutical Co., Ltd.) containing Tween 80] containing no test compound were orally administered to separate groups of the mice (0.1 ml per 10 g of body weight). One hour after the administration of the test compound, the forelimbs of each mouse and subsequently the hindlimbs of the same mouse were placed on a 4.5 cm-high, 1.0 cm-wide bar and catalepsy was estimated. All of the test compounds were orally administered at a dose of 10 mg/kg, and L-DOPA (100 mg/kg) and benserazide (25 mg/kg) were intraperitoneally administered together as a control experiment. The catalepsy score and the standard of judgment are shown below.

| score | duration of the cataleptic posture | |
|---|---|---|
| 0: | forelimbs | less than 5 seconds |
| | hindlimbs | less than 5 seconds |
| 1: | forelimbs | from 5 (inclusive) to 10 (exclusive) seconds |
| | hindlimbs | less than 5 seconds |
| 2: | forelimbs | 10 seconds or more |
| | hindlimbs | less than 5 seconds |
| 3: | forelimbs | from 5 (inclusive) to 10 (exclusive) seconds |
| | hindlimbs | from 5 (inclusive) to 10 (exclusive) seconds; |
| | or forelimbs | less than 5 seconds |
| | hindlimbs | 5 seconds or more |
| 4: | forelimbs | 10 seconds or more |
| | hindlimbs | from 5 (inclusive) to 10 (exclusive) seconds; |
| | or forelimbs | from 5 (inclusive) to 10 (exclusive) seconds |
| | hindlimbs | 10 seconds or more |
| 5: | forelimbs | 10 seconds or more |
| | hindlimbs | 10 seconds or more |

The effect of the compounds was evaluated by the total of the catalepsy scores of five mice in each group (25 points at the full). The groups wherein the total score was not more than 20 points were estimated to be effective. The number of the animals showing remission against catalepsy is the number of the mice for which the catalepsy score was not more than 4 points. The remission rate shows the rate of decrease in total score based on that of the control group.

The results are shown in Table 4.

TABLE 4

| Compound | Total Score | Number of the Animals Showing Remission | Remission Rate (%) |
|---|---|---|---|
| 0.3% Tween 80 (Control) | 25 | 0 | 0 |
| L-DOPA + benserazide | 18 | 4 | 28 |
| 3 | 20 | 5 | 20 |
| 4 | 11 | 5 | 56 |
| 6 | 19 | 4 | 24 |
| 7 | 11 | 4 | 56 |
| 10 | 17 | 3 | 32 |
| 11 | 19 | 2 | 24 |
| 12 | 15 | 3 | 40 |
| 24 | 7 | 5 | 72 |

Test Example 4

Effect on Clonidine-Induced Aggressive Behavior

The effect of a test compound on the aggressive behavior induced by intraperitoneal administration of clonidine was investigated [Eur. J. Pharmacol., 29, 374 (1968)].

The experiment was performed by using several groups of male ddY mice (weighing 20 to 25 g, Japan SLC), each group consisting of two mice. The test compound was suspended in injectable distilled water (Otsuka Pharmaceutical Co., Ltd.) containing Tween 80. Clonidine hydrochloride (Sigma Co.) was dissolved in physiological saline solution (Otsuka Pharmaceutical Co., Ltd.). The test compound suspension and the control suspension [injectable distilled water (Otsuka Pharmaceutical Co., Ltd.) containing Tween 80] were orally administered to separate groups of the mice (0.1 ml per 10 g of body weight). Sixty minutes after the oral administration of the test compound, clonidine hydrochloride (20 mg/kg) was intraperitoneally injected. The number of biting attacks during 30 minutes after clonidine treatment was counted. The effect of the compound was evaluated by comparing the average number of biting attacks of the test compound-administered groups with that of control groups (Student's t-test).

The results are shown in Table 5.

TABLE 5

| | | Number of the Biting Attacks (mean ± S.E.M.) | | Number of the Attacks of Test Compound- |
|---|---|---|---|---|
| Compd. | Dose (mg/kg, po) | Control Group (number of animals) | Test Compound-Treated Group (number of animals) | Treated Group/ Number of the Attacks of Control Group |
| 24 | 10 | 6.3 ± 2.09 (15) | 33.1 ± 7.16* (15) | 5.3 |

*:$p < 0.05$

Compounds (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

Injectable preparations can be prepared using a carrier such as distilled water, a salt solution, a glucose solution or a mixture of a salt solution and a glucose solution. The preparations can be prepared in the form of solution, suspension, or dispersion according to a conventional method by using a suitable solubilizing agent or suspending agent.

Compounds (I) and pharmaceutically acceptable salts thereof can be administered orally in the said dosage forms or parenterally as injections. The effective dose and the administration schedule vary depending upon the mode of administration, the age, body weight, and conditions of a patient, etc. However, generally, Compound (I) or a pharmaceutically acceptable salt thereof is administered in a daily dose of 0.01 to 25 mg/kg in 3 to 4 parts.

In addition, Compounds (I) may also be administered by inhalation in the form of aerosol, fine powder, or spray solution. In the case of aerosol administration, the compound of the present invention is dissolved in an appropriate pharmaceutically acceptable solvent such as ethyl alcohol or a combination of miscible solvents, and the resulting solution is mixed with a pharmaceutically acceptable propellant.

Certain embodiments of the invention are illustrated in the following examples, reference examples, and preparation examples.

EXAMPLE 1

(E)-4,5-Dimethoxy-β-(7-methyl-1,3-dipropylxanthin-8-yl)styrene-2-sulfonic acid (Compound 1)

(E)-8-(3,4-Dimethoxystyryl)-7-methyl-1,3-dipropylxanthine (WO92/06976) (2.41 g, 5.84 mmol) was dissolved in thionyl chloride (11 ml), and chlorosulfonic acid (1.17 ml, 17.53 mmol) was added dropwise thereto at 0° C. The resulting solution was stirred at room temperature for 30 minutes and then poured into ice-water cautiously. The precipitated crystals were collected by filtration, washed with water, and dried under reduced pressure to give 2.77 g (yield 93%) of Compound 1 as a yellow powder.

Melting Point: 191.5°–193.5° C.

Elemental Analysis: $C_{22}H_{28}N_4O_7S \cdot H_2O$ Calcd. (%): C, 51.76; H, 5.92; N, 10.97 Found (%): C, 51.71; H, 6.01; N, 10.75

IR (KBr) $v_{max}$ (cm$^{-1}$): 3750 (br), 1716, 1681, 1542, 1507

NMR (270MHz; DMSO-d$_6$) δ (ppm): 8.63(1H, d, J=16.3Hz), 7.42(1H, s), 7.37(1H, s), 7.05(1H, d, J=16.3Hz), 4.04(3H, s), 4.00(2H, t, J=7.4Hz), 3.87(3H, s), 3.84(2H, t, J=7.4Hz), 3.79(3H, s), 1.90–1.55(4H, m), 0.92–0.84 (6H, m)

FAB-MS: 493 (M+H)$^+$

EXAMPLE 2

(E)-N,N-Diethyl-4,5-dimethoxy-β-(7-methyl-1,3-dipropylxanthin-8-yl)styrene-2-sulfonamide (Compound 2)

Compound 1 (1.00 g, 1.96 mmol) obtained in Example 1 was dissolved in 20 ml of dimethylformamide. To the solution was dropwise added 0.29 ml (3.92 mmol) of thionyl chloride under ice-cooling, and the resulting mixture was stirred at room temperature for 10 minutes. After ice-cooling, 1.02 ml (9.80 mmol) of diethylamine was added dropwise to the mixture, and the resulting mixture was stirred at room temperature for one hour. The mixture was poured into 50 ml of water and extracted three times with 20 ml of chloroform. The extract was washed successively with water and a saturated aqueous solution of sodium chloride, and dried over anhydrous sodium sulfate, followed by evaporation under reduced pressure. The residue was purified by column chromatography (eluent: 65% ethyl acetate/hexane), followed by recrystallization from cyclohexane/toluene to give 320 mg (yield 30%) of Compound 2 as a pale yellow powder.

Melting Point: 227.1°–227.7° C.

Elemental Analysis: $C_{26}H_{37}N_5O_6S$ Calcd. (%): C, 57.02; H, 6.81; N, 12.79 Found (%): C, 56.94; H, 6.86; N, 12.87

IR (KBr) $v_{max}$ (cm$^{-1}$): 2962, 1696, 1658, 1595, 1543, 1510, 1440

NMR (270MHz; CDCl$_3$) δ (ppm): 8.46(1H, d, J=15.5Hz), 7.58(1H, s), 7.14(1H, s), 6.73(1H, d, J=15.5Hz), 4.08 (3H, s), 4.02 (3H, s), 3.98 (3H, s), 4.15–3.94 (4H, m), 3.32 (4H, q, J=7.3Hz), 1.88–1.60 (4H, m), 1.12(6H, t, J=7.3Hz), 1.00–0.87(6H, m)

FAB-MS: 548 (M+H)$^+$

EXAMPLE 3

(E)-N,N-Dipropyl-4,5-dimethoxy-β-(7-methyl-1,3-dipropylxanthin-8-yl)styrene-2-sulfonamide (Compound 3)

Substantially the same procedure as in Example 2 was repeated using 1.00 g (1.96 mmol) of Compound 1 obtained in Example 1 and 2.68 ml (19.6 mmol) of dipropylamine. The resulting crude crystals were recrystallized from cyclohexane/toluene to give 450 mg (yield 40%) of Compound 3 as a pale yellow powder.

Melting Point: 207.8°–208.5° C.

Elemental Analysis: $C_{28}H_{41}N_5O_6S$ Calcd. (%): C, 58.41; H, 7.18; N, 12.16 Found (%): C, 58.34; H, 7.45; N, 12.14

IR (KBr) $v_{max}$ (cm$^{-1}$): 2874, 1699, 1656, 1560, 1509

NMR (270MHz; CDCl$_3$) δ (ppm): 8.47(1H, d, J=15.8Hz), 7.57(1H, s), 7.13(1H, s), 6.73(1H, d, J=15.8Hz), 4.08(3H, s), 4.02(3H, s), 3.98(3H, s), 4.11–3.90 (4H, m), 3.19 (4H, t, J=7.9Hz), 1.90–1.45 (8H, m), 1.00–0.90(6H, m), 0.81(6H, t, J=7.3Hz)

FAB-MS: 576 (M+H)$^+$

EXAMPLE 4

(E)-4,5-Dimethoxy-β-(7-methyl-1,3-dipropylxanthin-8-yl)-2-piperidinosulfonylstyrene (Compound 4)

Substantially the same procedure as in Example 2 was repeated using 1.00 g (1.96 mmol) of Compound 1 obtained in Example 1 and 1.93 ml (19.6 mmol) of piperidine. The resulting crude crystals were recrystallized from dimethylsulfoxide/water to give 600 mg (yield 55%) of Compound 4 as a pale yellow powder.

Melting Point: 266.5°–268.2° C.

Elemental Analysis: $C_{27}H_{37}N_5O_6S$ Calcd. (%): C, 57.94; H, 6.66; N, 12.51 Found (%): C, 57.64; H, 6.84; N, 12.14

IR (KBr) $v_{max}$ (cm$^{-1}$): 1696, 1656, 1508

NMR (270MHz; CDCl$_3$) δ (ppm): 8.53(1H, d, J=15.8Hz), 7.53 (1H, s), 7.17 (1H, s), 6.77 (1H, d, J=15.8Hz), 4.10 (3H, s), 4.02 (3H, s), 3.97 (3H, s), 4.11–3.90 (4H, m), 3.20–3.10 (4H, m), 1.90–1.40(10H, m), 1.00–0.90 (6H, m)

FAB-MS: 560 (M+H)$^+$

EXAMPLE 5

(E)-4,5-Dimethoxy-β-(7-methyl-1,3-dipropylxanthin-8-yl)-2-(4-methylpiperazin-1-ylsulfonyl)styrene (Compound 5) fumarate Substantially the same procedure as in Example 2 was repeated using 1.00 g (1.96 mmol) of Compound 1 obtained in Example 1 and 1.08 ml (9.8 mmol) of 4-methylpiperazine. The resulting crude crystals were recrystallized from ethanol to give 390 mg (0.679 mmol; yield 35%) of Compound 5 as a pale yellow powder. This compound was dissolved in 15 ml of isopropanol, and a solution of 79 mg (0.679 mmol) of fumaric acid in isopropanol was added thereto. The precipitated crystals were collected by filtration and dried to give 329 mg of the fumarate of Compound 5 as a pale yellow powder.

Melting Point: 248.8°–250.0° C. (decomposition)

IR (KBr) $v_{max}$ (cm$^{-1}$): 3450 (br), 1695, 1654, 1545, 1508

NMR (270MHz; DMSO-d$_6$) δ (ppm): 8.39(1H, d, J=15.8Hz), 7.65(1H, s), 7.340(1H, s), 7.37(1H, d, J=15.8Hz), 4.07(3H, s), 4.00(3H, s), 3.99(2H, t, J=7.4Hz), 3.89(3H, s), 3.85(2H, t, J=7.6Hz), 3.45–2.30(11H, m), 1.75–1.50(4H, m), 0.90–0.80(6H, m)

FAB-MS: 575 (M+H)$^+$

EXAMPLE 6

(E)-N-[2-(Dimethylamino)ethyl]-N-methyl-4,5-dimethoxy-β-(7-methyl-1,3-dipropylxanthin-8-yl) styrene-2-sulfonamide (Compound 6)

Substantially the same procedure as in Example 2 was repeated using 500 mg (0.98 mmol) of Compound 1 obtained in Example 1 and 0.62 ml (4.9 mmol) of N,N,N'-trimethyl-ethylenediamine. The resulting crude crystals were recrystallized from cyclohexane/toluene to give 280 mg (yield 48%) of Compound 6 as yellow needles.

Melting Point: 199.1°–199.7° C.

Elemental Analysis: $C_{27}H_{40}N_6O_6S$ Calcd. (%): C, 56.23; H, 6.99; N, 14.57 Found (%): C, 55.82; H, 7.14; N, 14.19

IR (KBr) $v_{max}$ (cm$^{-1}$): 1696, 1657, 1511, 1441

NMR (270MHz; CDCl$_3$) δ (ppm): 8.50(1H, d, J=15.8Hz), 7.55 (1H, s), 7.15 (1H, s), 6.74 (1H, d, J=15.8Hz), 4.09(3H, s), 4.02(3H, s), 4.15–4.05(2H, m), 3.97 (3H, s), 4.00–3.90 (2H, m), 3.23(2H, t, J=7.0Hz), 2.89(3H, s), 2.47(2H, t, J=7.0Hz), 2.19(6H, s), 1.85–1.50(4H, m), 1.00–0.90(6H, m)

FAB-MS: 577 (M+H)$^+$

EXAMPLE 7

(E)-β-(7-Methyl-1,3-dipropylxanthin-8-yl)styrene-4-carboxylic acid methyl ester (Compound 7) and (Z)-β-(7-methyl-1,3-dipropylxanthin-8-yl)styrene-4-carboxylic acid methyl ester (Compound 8)

60% Sodium hydride (25.9 mg, 0.648 mmol) was added to a suspension of 353 mg (0.719 mmol) of (4-methoxycarbonylbenzyl)triphenylphosphonium bromide in 3 ml of tetrahydrofuran under ice-cooling in a stream of argon. The reaction mixture was heated at 50° C. for 20 minutes, and then ice-cooled, and 100 mg (0.360 mmol) of Compound c obtained in Reference Example 3 was added slowly thereto. The resulting mixture was stirred at room temperature for 30 minutes. The mixture was then poured into 10 ml of water and extracted three times with 10 ml of ether. The extract was washed with a saturated aqueous solution of sodium chloride, and dried over anhydrous sodium sulfate, followed by evaporation under reduced pressure. The residue was purified by column chromatography (eluent: 25% ethyl acetate/hexane) to give 40.0 mg (yield 27%) of Compound 7 and 39.5 mg (yield 27%) of Compound 8 as pale yellow powders.

Compound 7

NMR (270MHz; CDCl$_3$) δ (ppm): 8.07(2H, d, J=8.4Hz), 7.82(1H, d, J=15.8Hz), 7.67(2H, d, J=8.4Hz), 7.01 (1H, d, J=15.8Hz), 4.11(2H, t, J=7.4Hz), 4.09(3H, s), 3.95(2H, t, J=7.1Hz), 3.94 (3H, s), 1.91–1.60 (4H, m), 1.00–0.90(6H, m)

EI-MS: 410 (M)$^+$

Compound 8

NMR (270MHz; CDCl$_3$) δ (ppm): 7.97(2H, d, J=8.4Hz), 7.54(2H, d, J=8.4Hz), 7.03(1H, d, J=12.4Hz), 6.47 (1H, d, J=12.4Hz), 4.05–3.90(4H, m), 3.92(3H, s), 3.78(3H, s), 1.85–1.60(4H, m), 1.05–0.90(6H, m)

EI-MS: 410 (M)$^+$

EXAMPLE 8

(E)-4,5-Dimethoxy-β-(7-methyl-1,3-dipropylxanthin-8-yl)styrene-2-sulfonamide (Compound 9)

Substantially the same procedure as in Example 2 was repeated using 1.00 g (1.96 mmol) of Compound 1 obtained in Example 1 and 0.6 ml of conc. aqueous ammonia. The resulting crude crystals were recrystallized from dioxane/water to give 670 mg (yield 70%) of Compound 9 as yellow needles.

Melting Point: 266.1°–267.8° C.

Elemental Analysis: $C_{22}H_{29}N_5O_6S.H_2O$ Calcd. (%): C, 51.85; H, 6.13; N, 13.74 Found (%): C, 51.99; H, 6.10; N, 13.48

IR (KBr) $v_{max}$ (cm$^{-1}$): 1695, 1654, 1510

NMR (270MHz; DMSO-d$_6$) δ (ppm): 8.40(1H, d, J=15.8Hz), 7.50(1H, s), 7.48(1H, s), 7.45(2H, s), 7.23(1H, d, J=15.8Hz), 4.05(3H, s), 3.95(3H, s), 3.85(3H, s), 4.10–3.80 (4H, m), 1.75–1.51(4H, m), 0.89(3H, t, J=7.3Hz), 0.87(3H, t, J=7.3Hz)

FAB-MS: 492 (M+H)$^+$

EXAMPLE 9

(E)-N-Phenyl-4,5-dimethoxy-β-(7-methyl-1,3-dipropylxanthin-8-yl)styrene-2-sulfonamide (Compound 10)

Substantially the same procedure as in Example 2 was repeated using 1.00 g (1.96 mmol) of Compound 1 obtained in Example 1 and 1.85 ml (20.3 mmol) of aniline. The resulting crude crystals were recrystallized from toluene to give 261 mg (yield 23%) of Compound 10 as a pale yellow powder.

Melting Point: 247.4°–249.1° C.

Elemental Analysis: $C_{28}H_{33}N_5O_6S$ Calcd. (%): C, 59.24; H, 5.86; N, 12.34 Found (%): C, 59.17; H, 5.88; N, 12.18

IR (KBr) $v_{max}$ (cm$^{-1}$): 1695, 1657, 1509

NMR (270MHz; DMSO-d$_6$) δ (ppm): 10.25(1H, brs), 8.34 (1H, d, J=15.5Hz), 7.39(2H, s), 7.18–7.05(5H, m), 6.98–6.93(1H, m), 4.04(2H, t, J=7.0Hz), 4.00(3H, s), 3.92 (3H, s), 3.86(2H, t, J=7.3Hz), 3.77(3H, s), 1.81–1.52(4H, m), 0.92(3H, t, J=7.3Hz), 0.88 (3H, t, J=7.3Hz)

FAB-MS: 568 (M+H)$^+$

EXAMPLE 10

(E)-β-(7-Methyl-1,3-dipropylxanthin-8-yl)-3,4,5-trimethoxystyrene-2-sulfonic acid (Compound 11)

Substantially the same procedure as in Example 1 was repeated using 10.0 g (22.6 mmol) of (E)-7-methyl-1,3-dipropyl-8-(3,4,5-trimethoxystyryl)xanthine (WO92/06976). The resulting crude crystals were recrystallized from acetonitrile to give 3.83 g (yield 32%) of Compound 11 as a pale yellow powder.

Melting Point: 247.9°–249.6° C.

Elemental Analysis: $C_{23}H_{30}N_4O_8S.1.5H_2O$ Calcd. (%): C, 50.26; H, 6.05; N, 10.19 Found (%): C, 50.53; H, 6.06; N, 10.32

IR (KBr) $v_{max}$ (cm$^{-1}$): 1719, 1681

NMR (270MHz; DMSO-d$_6$) δ (ppm): 8.80(1H, d, J=15.8Hz), 7.03(1H, s), 6.84(1H, d, J=15.8Hz), 4.02(3H, s), 3.89(3H, s), 3.76(3H, s), 3.74(3H, s), 4.05–3.90 (2H, m), 3.86–3.73(2H, m), 1.79–1.53(4H, m), 0.91–0.84 (6H, m)

FAB-MS: 523 (M+H)$^+$

EXAMPLE 11

(E)-β-(7-Methyl-1,3-dipropylxanthin-8-yl)-3,4,5-trimethoxystyrene-2-sulfonamide (Compound 12)

Substantially the same procedure as in Example 2 was repeated using 1.80 g (3.45 mmol) of Compound 11 obtained in Example 10 and 1.0 ml of conc. aqueous ammonia. The resulting crude crystals were recrystallized from acetonitrile to give 200 mg (yield 11%) of Compound 12 as yellow needles.

Melting Point: 242.9°–244.7° C.

Elemental Analysis: $C_{23}H_{31}N_5O_7S$ Calcd. (%): C, 52.96; H, 5.99; N, 13.43 Found (%): C, 52.89; H, 5.86; N, 13.11

IR (KBr) $v_{max}$ (cm$^{-1}$): 1692, 1648, 1496

NMR (270MHz; DMSO-$d_6$) δ (ppm): 8.59(1H, d, J=15.5Hz), 7.16(2H, s), 7.14(1H, s), 7.02(1H, d, J=15.5Hz), 4.03(3H, s), 3.98(3H, s), 3.91(3H, s), 3.83(3H, s), 4.05–3.90 (2H, m), 3.85–3.70(2H, m), 1.79–1.50 (4H, m), 0.91–0.84 (6H, m)

FAB-MS: 522 (M+H)$^+$

EXAMPLE 12

(E)-N-[2-(Dimethylamino)ethyl]-N-methyl-β-(7-methyl-1,3-dipropylxanthin-8-yl)-3,4,5-trimethoxystyrene-2-sulfonamide (Compound 13) fumarate Substantially the same procedure as in Example 2 was repeated using 1.40 g (2.68 mmol) of Compound 11 obtained in Example 10 and 0.39 ml (5.36 mmol) of N,N,N'-trimethylethylenediamine. The resulting crude crystals (670 mg) was dissolved in 10 ml of isopropanol, and 97 mg (0.84 mmol) of fumaric acid was added thereto. The precipitated crystals were collected by filtration and dried to give 550 mg (yield 28%) of the fumarate of Compound 13 as a yellow powder.

Melting Point: 191.6°–192.9° C.

Elemental Analysis: $C_{28}H_{42}N_6O_7S \cdot C_4H_4O_4$ Calcd. (%): C, 53.17; H, 6.41; N, 11.63 Found (%): C, 53.43; H, 6.34; N, 11.64

IR (KBr) $v_{max}$ (cm$^{-1}$): 1695, 1650

NMR (270MHz; DMSO-$d_6$) δ (ppm): 8.44(1H, d, J=15.5Hz), 7.17(1H, s), 7.03(1H, d, J=15.5Hz), 6.59(2H, s), 4.03(3H, s), 3.99(3H, s), 3.88(3H, s), 3.83(3H, s), 4.05–3.90 (2H, m), 3.85–3.70 (2H, m), 3.21 (2H, t, J=6.6Hz), 2.80 (3H, s), 2.47 (2H, t, J=6.6Hz), 2.19(6H, s), 1.80–1.48(4H, m), 0.91–0.84(6H, m)

FAB-MS: 607 (M+H)$^+$

EXAMPLE 13

(E)-N-(2-Hydroxyethyl)-4,5-dimethoxy-β-(7-methyl-1,3-dipropylxanthin-8-yl)styrene-2-sulfonamide (Compound 14)

Substantially the same procedure as in Example 2 was repeated using 1.00 g (1.96 mmol) of Compound 1 obtained in Example 1 and 1.2 ml (20.3 mmol) of ethanolamine. The resulting crude crystals were recrystallized from toluene to give 600 mg (yield 55%) of Compound 14 as yellow plates.

Melting Point: 213.4°–215.0° C.

Elemental Analysis: $C_{24}H_{33}N_5O_7S$ Calcd. (%): C, 53.82; H, 6.21; N, 13.08 Found (%): C, 54.03; H, 6.31; N, 12.89

IR (KBr) $v_{max}$ (cm$^{-1}$): 1700, 1655, 1510

NMR (270MHz; DMSO-$d_6$) δ (ppm): 8.45(1H, d, J=15.5Hz), 7.60(1H, brs), 7.53(1H, s), 7.44(1H, s), 7.25(1H, d, J=15.5Hz), 4.70(1H, t, J=5.2Hz), 4.05(3H, s), 3.96(3H, s), 3.86(3H, s), 4.10–3.80(4H, m), 3.40–3.32(1H, m), 2.95(1H, t, J=6.0Hz), 1.78–1.50(4H, m), 0.92–0.84 (6H, m)

FAB-MS: 536 (M+H)$^+$

EXAMPLE 14

(E) -4,5-Dimethyl-β-(7-methyl-1,3-dipropylxanthin-8-yl)styrene-2-sulfonic acid (Compound 15)

Substantially the same procedure as in Example 1 was repeated using 4.9 g (12.9 mmol) of (E)-8-(3,4-dimethylstyryl)-7-methyl-1,3-dipropylxanthine (WO92/06976). The resulting crude crystals were recrystallized from ethanol to give 3.09 g (yield 67%) of Compound 15 as a pale yellow powder.

Melting Point: >280° C.

Elemental Analysis: $C_{22}H_{28}N_4O_5S \cdot H_2O$ Calcd. (%): C, 55.22; H, 6.32; N, 11.71 Found (%): C, 55.37; H, 6.42; N, 11.76

IR (KBr) $v_{max}$ (cm$^{-1}$): 1719, 1679

NMR (270MHz; DMSO-$d_6$) δ (ppm): 8.61(1H, d, J=15.8Hz), 7.67(1H, s), 7.59(1H, s), 7.07(1H, d, J=15.8Hz), 4.03(3H, s), 4.00(2H, t, J=7.2Hz), 3.85(2H, t, J=7.0Hz), 2.27(3H, s), 2.24(3H, s), 1.80–1.50(4H, m), 0.89(3H, t, J=7.3Hz), 0.87(3H, t, J=7.2Hz)

FAB-MS: 461 (M+H)$^+$

EXAMPLE 15

(E)-β-(1,3-Diethyl-7-methylxanthin-8-yl)-5-methoxystyrene-2-sulfonic acid (Compound 16)

Substantially the same procedure as in Example 1 was repeated using 4.0 g (11.3 mmol) of Compound s obtained in Reference Example 18. The resulting crude crystals were recrystallized from dioxane/water to give 3.27 g (yield 34%) of Compound 16 as pale yellow plates.

Melting Point: 208.9°–210.5° C.

Elemental Analysis: $C_{19}H_{22}N_4O_6S \cdot H_2O$ Calcd. (%): C, 50.43; H, 5.35; N, 12.38 Found (%): C, 50.13; H, 5.36; N, 12.34

IR (KBr) $v_{max}$ (cm$^{-1}$): 1714, 1673, 1652, 1560

NMR (270MHz; DMSO-$d_6$) δ (ppm): 8.65(1H, d, J=15.8Hz), 7.77(1H, d, J=8.6Hz), 7.37(1H, d, J=2.6Hz), 7.14 (1H, d, J=15.8Hz), 6.87(1H, dd, J=8.6, 2.6Hz), 4.08 (2H, q, J=6.9Hz), 3.93(2H, q, J=7.2Hz), 3.84 (3H, s), 1.27(3H, t, J=6.9Hz), 1.14(3H, t, J=7.2Hz)

EI-MS: 434 (M)$^+$

EXAMPLE 16

(E)-β-(1,3-Diethyl-7-methylxanthin-8-yl)-5-methoxystyrene-2-sulfonamide (Compound 17)

Substantially the same procedure as in Example 2 was repeated using 1.00 g (2.30 mmol) of Compound 16 obtained in Example 15 and 0.7 ml of conc. aqueous ammonia. The resulting crude crystals were purified by high performance liquid chromatography (column: YMC-pack, SH-365-10, 30 i.d.×500 mm, eluent: 40% acetonitrile/water, flow rate: 40 ml/min) to give 55 mg (yield 6%) of Compound 17 as a pale yellow powder.

Melting Point: 236.5°–237.2° C.

Elemental Analysis: $C_{19}H_{23}N_5O_5S \cdot 0.5H_2O$ Calcd. (%): C, 51.57; H, 5.47; N, 15.83 Found (%): C, 51.86; H, 5.30; N, 15.76

IR (KBr) $v_{max}$ (cm$^{-1}$): 1700, 1659

NMR (270MHz; DMSO-$d_6$) δ (ppm): 8.41(1H, d, J=15.5Hz), 7.87(1H, d, J=8.6Hz), 7.53(1H, d, J=2.3Hz), 7.44 (2H, brs), 7.31(1H, d, J=15.8Hz), 7.10(1H, dd, J=8.6, 2.3Hz), 4.06(3H, s), 4.10–4.00(2H, m), 3.95–3.85(2H, m), 3.91(3H, s), 1.27(3H, t, J=6.9Hz), 1.14 (3H, t, J=7.2Hz)

FAB-MS: 434 (M+H)$^+$

EXAMPLE 17

(Z)-β-(7-Methyl-1,3-dipropylxanthin-8-yl)styrene-4-carboxylic acid (Compound 18)

Compound 8 (2.64 g, 6.44 mmol) obtained in Example 7 was dissolved in a solvent mixture of 60 ml of dioxane and 40 ml of water. To the solution was added 1.08 g (25.8 mmol) of lithium hydroxide monohydrate, and the resulting mixture was stirred at room temperature for one hour. After neutralization with 1N HCl, the mixture was extracted three times with ethyl acetate. The combined extract was dried over anhydrous sodium sulfate, followed by evaporation under reduced pressure. The resulting crude crystals were recrystallized from toluene/cyclohexane to give 2.26 g (yield 89%) of Compound 18 as a yellow powder.

Melting Point: 214.7°–216.9° C.

Elemental Analysis: $C_{21}H_{24}N_4O_4 \cdot 0.1CH_3C_6H_5$ Calcd. (%): C, 64.25; H, 6.16; N, 13.81 Found (%): C, 64.34; H, 6.33; N, 13.91

IR (KBr) $v_{max}$ (cm$^{-1}$): 1723, 1687, 1656

NMR (270MHz; DMSO-d$_6$) δ (ppm): 7.87(2H, d, J=8.6Hz), 7.76(2H, d, J=8.6Hz), 7.08(1H, d, J=12.5Hz), 6.70 (1H, d, J=12.5Hz), 3.87(3H, s), 3.90–3.77(4H, m), 1.66–1.49(4H, m), 0.86(3H, t, J=7.6Hz), 0.79(3H, t, J=7.6Hz)

EI-MS: 396 (M)$^+$

EXAMPLE 18

(E)-β-(7-Methyl-1,3-dipropylxanthin-8-yl)styrene-4-carboxylic acid (Compound 19)

A solution of 1.25 g (3.15 mmol) of Compound 18 obtained in Example 17 and 40 mg (0.32 mmol) of iodine in 125 ml of toluene was heated under reflux for 6.5 hours. After cooling, a 0.1M aqueous solution of sodium thiosulfate and chloroform were added thereto, followed by stirring. The precipitated crystals were collected by filtration, and recrystallized from ethanol to give 740 mg (yield 59%) of Compound 19 as ocher needles.

Melting Point: 273.4°–275.4° C.

Elemental Analysis: $C_{21}H_{24}N_4O_4$ Calcd. (%): C, 63.62; H, 6.10; N, 14.13 Found (%): C, 63.49; H, 6.25; N, 14.12

IR (KBr) $v_{max}$ (cm$^{-1}$): 1726, 1691, 1633, 1543

NMR (270MHz; DMSO-d$_6$) δ (ppm): 7.96(2H, d, J=8.2Hz), 7.90(2H, d, J=8.2Hz), 7.70(1H, d, J=15.5Hz), 7.47 (1H, d, J=15.5Hz), 4.06(3H, s), 4.02(2H, t, J=6.8Hz), 3.84(2H, t, J=7.0Hz), 1.81–1.49(4H, m), 0.92–0.80 (6H, m)

EI-MS: 396 (M)$^+$

EXAMPLE 19

(E)-β-(1,3-Diethyl-7-methylxanthin-8-yl)-2-methoxystyrene-4-carboxylic acid methyl ester (Compound 20)

A 1.65M n-butyl lithium/hexane solution (1.09 ml, 1.799 mmol) was added to a suspension of 938 mg (1.799 mmol) of (2-methoxy-4-methoxycarbonylbenzyl)triphenylphosphonium bromide in 10 ml of tetrahydrofuran under ice-cooling in an argon atmosphere. The reaction mixture was stirred at room temperature for 30 minutes, and ice-cooled, and a suspension of 300 mg (1.199 mmol) of Compound f obtained in Reference Example 6 in 1 ml of tetrahydrofuran was added slowly thereto. The resulting solution was stirred at room temperature for 2.5 hours. After ice-cooling, 1.8 ml of a 1 N aqueous solution of ammonium chloride was added thereto, followed by addition of ethyl acetate. The organic layer was washed three times with a saturated aqueous solution of sodium chloride, and dried over anhydrous sodium sulfate, followed by evaporation under reduced pressure. The residue was purified by column chromatography (eluent: hexane/ethyl acetate=3/1) to give 422 mg (yield 85%) of Compound 20, which was further recrystallized from hexane/ethyl acetate to give a yellow powder.

Melting Point: 239.0°–241.2° C.

Elemental Analysis: $C_{21}H_{24}N_4O_5$ Calcd. (%): C, 61.16; H, 5.86; N, 13.58 Found (%): C, 61.28; H, 5.99; N, 13.62

IR (KBr) $v_{max}$ (cm$^{-1}$): 1719, 1687, 1652, 1304, 1231

NMR (270MHz; CDCl$_3$) δ (ppm): 8.02(1H, d, J=15.8Hz), 7.69–7.59(3H, m), 7.18(1H, d, J=15.8Hz), 4.23(2H, q, J=7.3Hz), 4.09(2H, q, J=7.3Hz), 4.07(3H, s), 4.01(3H, s), 3.95(3H, s), 1.39(3H, t, J=7.3Hz), 1.27(3H, t, J=7.3Hz)

EXAMPLE 20

(E)-2-Methoxy-β-(7-methyl-1,3-dipropylxanthin-8-yl)styrene-4-carboxylic acid methyl ester (Compound 21)

Substantially the same procedure as in Example 19 was repeated using 2.81 g (5.390 mmol) of (2-methoxy-4-methoxycarbonylbenzyl)triphenylphosphonium bromide, 3.27 ml (5.396 mmol) of a 1.65M n-butyl lithium/hexane solution, and 1.00 g (3.593 mmol) of Compound c obtained in Reference Example 3. The resulting crude crystals were recrystallized from hexane/ethyl acetate to give 203 mg (yield 33%) of Compound 21 as yellow grains.

Melting Point: 198.5°–200.4° C.

Elemental Analysis: $C_{23}H_{28}N_4O_5 \cdot 0.4H_2O$ Calcd. (%): C, 61.70; H, 6.48; N, 12.51 Found (%): C, 61.77; H, 6.42; N, 12.45

IR (KBr) $v_{max}$ (cm$^{-1}$): 1704, 1655, 1541, 1436, 1234

NMR (270MHz; CDCl$_3$) δ (ppm): 8.00(1H, d, J=15.8Hz), 7.69–7.59(3H, m), 7.19(1H, d, J=15.8Hz), 4.15–3.98(4H, m), 4.06(3H, s), 4.01(3H, s), 3.94(3H, s), 1.88–1.65 (4H, m), 1.00 (3H, t, J=7.6Hz), 0.97 (3H, t, J=7.6Hz)

EXAMPLE 21

(E)-β-(1,3-Diethyl-7-methylxanthin-8-yl)-2-methoxystyrene-4-carboxylic acid (Compound 22)

Compound 20 (108 mg, 0.262 mmol) obtained in Example 19 was suspended in a solvent mixture of 2 ml of tetrahydrofuran, 2 ml of ethanol, and 1 ml of water. To the suspension was added 55 mg (1.311 mmol) of lithium hydroxide monohydrate, and the resulting mixture was stirred at room temperature for 12 hours. The reaction mixture was acidified with 2N HCl, and the precipitated crystals were collected by filtration. The obtained crude crystals were purified by column chromatography (eluent: chloroform/methanol/acetic acid=40/1/1) to give 25 mg (yield 24%) of Compound 22, which was further recrystallized from isopropanol to give a yellow powder.

Melting Point: >280° C.

Elemental Analysis: $C_{20}H_{22}N_4O_5 \cdot 0.6H_2O$ Calcd. (%): C, 58.70; H, 5.71; N, 13.69 Found (%): C, 58.55; H, 5.66; N, 13.46

IR (KBr) $v_{max}$ (cm$^{-1}$): 1689, 1648, 1543, 1434, 1305

NMR (270MHz; DMSO-d$_6$) δ (ppm): 8.00(1H, d, J=8.3Hz), 7.94 (1H, d, J=15.8Hz), 7.58 (1H, d, J=8.3Hz), 7.56 (1H, s), 7.44(1H, d, J=15.8Hz), 4.07(2H, q, J=6.9Hz), 4.04 (3H, s), 3.96 (3H, s), 3.92 (2H, q, J=6.9Hz), 1.27(3H, t, J=6.9Hz), 1.13(3H, t, J=6.9Hz)

EXAMPLE 22

(E)-2-Methoxy-β-(7-methyl-1,3-dipropylxanthin-8-yl)styrene-4-carboxylic acid (Compound 23)

Substantially the same procedure as in Example 21 was repeated using 300 mg (0.681 mmol) of Compound 21 obtained in Example 20. The resulting crude crystals were recrystallized from isopropanol to give 203 mg (yield 70%) of Compound 23 as a yellow powder.

Melting Point: 284.7°–286.1° C.

Elemental Analysis: $C_{22}H_{26}N_4O_5$ Calcd. (%): C, 61.96; H, 6.14; N, 13.14 Found (%): C, 61.74; H, 6.31; N, 13.12

IR (KBr) $v_{max}$ (cm$^{-1}$): 2864, 1691, 1650, 1531, 1435

NMR (270MHz; DMSO-$d_6$) δ (ppm): 13.04(1H, brs), 7.98 (1H, d, J=7.9Hz), 7.91(1H, d, J=15.8Hz), 7.57(1H, d, J=7.9Hz), 7.56(1H, s), 7.42(1H, d, J=15.8Hz), 4.03(3H, s), 4.00(2H, t, J=7.3Hz), 3.96(3H, s), 3.83(2H, t, J=7.3Hz), 1.80–1.67(2H, m), 1.63–1.50 (2H, m), 0.91(3H, t, J=7.3Hz), 0.87(3H, t, J=7.3Hz)

EXAMPLE 23

(E)-8-(3-Acetylstyryl)-1,3-diethyl-7-methylxanthine (Compound 24)

Compound h (1.00 g, 2.480 mmol) obtained in Reference Example 8 and dichlorobis(triphenylphosphine)palladium (17 mg, 0.024 mmol) were suspended in 20 ml of dimethylformamide. To the suspension was added 0.84 ml (2.486 mmol) of (1-ethoxyvinyl)tributyltin in an argon atmosphere, and the resulting mixture was stirred at 120° C. for 3 hours. After ice-cooling, 2N ammonium fluoride was added to the mixture, followed by filtration. The filtrate was diluted with chloroform, and washed with a saturated aqueous solution of sodium chloride, and the organic layer was dried over anhydrous sodium sulfate, followed by evaporation under reduced pressure. The residue was suspended in a solvent mixture of 20 ml of tetrahydrofuran and 5 ml of 2N HCl, and the suspension was stirred at room temperature for 2.5 hours. After neutralization with a 2N aqueous solution of sodium hydroxide, the reaction mixture was diluted with chloroform. The organic layer was washed with a saturated aqueous solution of sodium chloride, and dried over anhydrous sodium sulfate, followed by evaporation under reduced pressure. The residue was purified by column chromatography (eluent: hexane/ethyl acetate=2/1), and further recrystallized from ethyl acetate to give 482 mg (yield 53%) of Compound 24 as pale yellow flocculent precipitates.

Melting Point: 221.4°–221.8° C.

Elemental Analysis: $C_{20}H_{22}N_4O_3$ Calcd. (%): C, 65.56; H, 6.05; N, 15.29 Found (%): C, 65.23; H, 6.22; N, 15.26

IR (KBr) $v_{max}$ (cm$^{-1}$): 1679, 1650, 1542, 1441, 1276

NMR (270MHz; CDCl$_3$) δ (ppm): 8.19(1H, s), 7.93(1H, d, J=7.9Hz), 7.84(1H, d, J=15.8Hz), 7.77(1H, d, J=7.9Hz), 7.52(1H, t, J=7.9Hz), 7.01(1H, d, J=15.8Hz), 4.22 (2H, q, J=6.9Hz), 4.10 (2H, q, J=6.9Hz), 4.09(3H, s), 2.66(3H, s), 1.39(3H, t, J=6.9Hz), 1.27 (3H, t, J=6.9Hz)

EXAMPLE 24

(E)-β-(1,3-Diethyl-7-methylxanthin-8-yl) styrene-3-carboxylic acid (Compound 25)

Sodium hydroxide (432 mg, 10.8 mmol) and bromine (0.13 ml, 2.523 mmol) were added to water (3 ml) under ice-cooling, followed by addition of dioxane (3 ml). The mixture was slowly added to a suspension of 300 mg (0.819 mmol) of Compound 24 obtained in Example 23 in 3 ml of dioxane under ice-cooling, and the resulting mixture was stirred at room temperature for 3.5 hours. After ice-cooling, a 5% aqueous solution of sodium thiosulfate was added thereto, and the mixture was acidified with 2N HCl. The precipitated crystals were collected by filtration, and recrystallized from ethanol/water to give 254 mg (yield 84%) of Compound 25 as pale yellow needles.

Melting Point: 260.2°–261.5° C.

Elemental Analysis: $C_{19}H_{20}N_4O_4$·0.3$H_2O$ Calcd. (%): C, 61.05; H, 5.55; N, 14.99 Found (%): C, 60.99; H, 5.49; N, 14.89

IR (KBr) $v_{max}$ (cm$^{-1}$): 1688, 1652, 1541, 1436, 1281, 1258

NMR (270MHz; DMSO-$d_6$) δ (ppm): 13.09(1H, brs), 8.32 (1H, s), 8.03(1H, d, J=7.9Hz), 7.92(1H, d, J=7.6Hz), 7.73(1H, d, J=15.8Hz), 7.55(1H, d, J=7.9, 7.6Hz), 7.45(1H, d, J=15.8Hz), 4.08(2H, q, J=6.9Hz), 4.06(3H, s), 3.92(2H, q, J=6.9Hz), 1.27 (3H, t, J=6.9Hz), 1.13(3H, t, J=6.9Hz)

EXAMPLE 25

(E)-8-(3-Acetyl-4-methoxystyryl)-7-methyl-1,3-dipropylxanthine (Compound 26)

Substantially the same procedure as in Example 23 was repeated using 1.00 g (2.168 mmol) of Compound j obtained in Reference Example 10, 15 mg (0.021 mmol) of dichlorobis(triphenylphosphine) palladium, and 0.74 ml (2.190 mmol) of (1-ethoxyvinyl)tributyltin. The resulting crude crystals were recrystallized from ethyl acetate to give 407 mg (yield 44%) of Compound 26 as pale yellow needles.

Melting Point: 193.9°–194.7° C.

Elemental Analysis: $C_{23}H_{28}N_4O_4$ Calcd. (%): C, 65.08; H, 6.64; N, 13.20 Found (%): C, 65.11; H, 6.71; N, 13.23

IR (KBr) $v_{max}$ (cm$^{-1}$): 1694, 1657, 1501, 1439, 1267

NMR (270MHz; CDCl$_3$) δ (ppm): 8.02(1H, d, J=2.3Hz), 7.75(1H, d, J=15.8Hz), 7.66(1H, dd, J=8.6, 2.3Hz), 7.01(1H, d, J=8.6Hz), 6.85(1H, d, J=15.8Hz), 4.13–3.95(4H, m), 4.05(3H, s), 3.97(3H, s), 2.65(3H, s), 1.90–1.65(4H, m), 1.00(3H, t, J=7.6Hz), 0.97 (3H, t, J=7.6Hz)

EXAMPLE 26

(E)-4-Methoxy-β-(7-methyl-1,3-dipropylxanthin-8-yl)styrene-3-carboxylic acid (Compound 27)

Substantially the same procedure as in Example 24 was repeated using 200 mg (0.471 mmol) of Compound 26 obtained in Example 25. The resulting crude crystals were recrystallized from dioxane/water to give 190 mg (yield 95%) of Compound 27 as a yellow powder.

Melting Point: 209° C. (decomposition)

IR (KBr) $v_{max}$ (cm$^{-1}$): 1687, 1657, 1543, 1503, 1262

NMR (270MHz; DMSO-$d_6$) δ (ppm): 12.78(1H, brs), 8.05 (1H, d, J=2.3Hz), 7.89(1H, dd, J=8.6, 2.3Hz), 7.62 (1H, d, J=15.8Hz), 7.26(1H, d, J=15.8Hz), 7.17(1H, d, J=8.6Hz), 4.02(3H, s), 3.99(2H, t, J=7.3Hz), 3.87(3H, s), 3.83(2H, t, J=7.3Hz), 1.77–1.53(4H, m), 0.90(3H, t, J=7.3Hz), 0.87(3H, t, J=7.3Hz)

FAB-MS: 427 (M+H)$^+$

EXAMPLE 27

(E)-8-(3-Acetyl-4-fluorostyryl)-1,3-diethyl-7-methylxanthine (Compound 28)

Substantially the same procedure as in Example 23 was repeated using 500 mg (1.187 mmol) of Compound m obtained in Reference Example 12, 10 mg (0.014 mmol) of dichlorobis(triphenylphosphine)palladium, and 0.41 ml (1.214 mmol) of (1-ethoxyvinyl)tributyltin. The resulting crude crystals were recrystallized from ethyl acetate to give 174 mg (yield 61%) of Compound 28 as yellow needles.

Melting Point: 238.1°–239.3° C.

Elemental Analysis: $C_{20}H_{21}FN_4O_3 \cdot 0.6H_2O$ Calcd. (%): C, 60.78; H, 5.66; N, 14.18 Found (%): C, 60.50; H, 5.42; N, 14.31

IR (KBr) $v_{max}$ (cm$^{-1}$): 1684, 1657, 1652, 1541, 1437

NMR (270MHz; CDCl$_3$) δ (ppm): 8.13(1H, dd, J=6.9, 2.3Hz), 7.78(1H, d, J=15.8Hz), 7.74–7.68(1H, m), 7.20(1H, dd, J=10.6, 8.6Hz), 6.92(1H, d, J=15.8Hz), 4.21(2H, q, J=6.9Hz), 4.09(2H, q, J=6.9Hz), 4.08(3H, s), 2.69(3H, d, J=5.0Hz), 1.38 (3H, t, J=6.9Hz), 1.27(3H, t, J=6.9Hz)

EXAMPLE 28

(E)-β-(1,3-Diethyl-7-methylxanthin-8-yl)-4-fluorostyrene-3-carboxylic acid (Compound 29)

Substantially the same procedure as in Example 24 was repeated using 450 mg (1.165 mmol) of Compound 28 obtained in Example 27. The resulting crude crystals were recrystallized from ethanol to give 187 mg (yield 41%) of Compound 29 as a pale brown powder.

Melting Point: 247° C. (decomposition)

IR (KBr) $v_{max}$ (cm$^{-1}$): 1695, 1658, 1547, 1538, 1440

NMR (270MHz; DMSO-d$_6$) δ (ppm): 8.18–8.15(1H, m), 8.00–7.90(1H, m), 7.67(1H, d, J=15.8Hz), 7.35–7.28(1H, m), 7.33(1H, d, J=15.8Hz), 4.06(2H, q, J=6.9Hz), 4.02(3H, s), 3.91(2H, q, J=6.9Hz), 1.25(3H, t, J=6.9Hz), 1.13 (3H, t, J=6.9Hz)

FAB-MS: 387 (M+H)$^+$

EXAMPLE 29

(E)-8-(4-Acetyl-3-methoxystyryl)-1,3-diethyl-7-methylxanthine (Compound 30)

Substantially the same procedure as in Example 23 was repeated using 200 mg of crude Compound q obtained in Reference Example 16, 6 mg (0.009 mmol) of dichlorobis(triphenylphosphine)palladium, and 0.27 ml (0.799 mmol) of (1-ethoxyvinyl)tributyltin to give 50 mg (yield 32% of Compound 30, which was further recrystallized from ethyl acetate to give yellow needles.

Melting Point: 236.1°–237.2° C.

Elemental Analysis: $C_{21}H_{24}N_4O_4 \cdot 0.3H_2O$ Calcd. (%): C, 62.77; H, 6.17; N, 13.94 Found (%): C, 62.90; H, 6.16; N, 13.79

IR (KBr) $v_{max}$ (cm$^{-1}$): 1697, 1655, 1594, 1543, 1409

NMR (270MHz; CDCl$_3$) δ (ppm): 7.80(1H, d, J=8.3Hz), 7.78(1H, d, J=15.8Hz), 7.26(1H, d, J=8.3Hz), 7.10 (1H, s), 6.99(1H, d, J=15.8Hz), 4.22(2H, q, J=6.9Hz), 4.09(2H, q, J=6.9Hz), 4.09(3H, s), 3.99 (3H, s), 2.63(3H, s), 1.39(3H, t, J=6.9Hz), 1.27 (3H, t, J=6.9Hz)

EXAMPLE 30

(E)-β-(7-Methyl-1,3-dipropylxanthin-8-yl)styrene-4-sulfonic acid (Compound 31)

(E)-7-Methyl-1,3-dipropyl-8-styrylxanthine (WO92/06976) (500 mg, 1.42 mmol) was dissolved in chloroform (5 ml), and chlorosulfonic acid (0.28 ml, 4.26 mmol) was added dropwise thereto at 0° C. The resulting solution was heated under reflux for 3 hours and then poured into 20 ml of ice-water. The chloroform layer was separated and the aqueous layer was extracted 5 times with tetrahydrofuran. The combined organic layer was dried over anhydrous magnesium sulfate, and the solvent was evaporated under reduced pressure to give 240 mg (yield 39%) of Compound 31 as a pale yellow powder.

Melting Point: >270° C.

IR (KBr) $v_{max}$ (cm$^{-1}$): 3400 (br), 1676, 1543

NMR (270MHz; DMSO-d$_6$) δ (ppm): 7.77(2H, d, J=8.4Hz), 7.66(1H, d, J=15.8Hz), 7.65(2H, d, J=8.4Hz), 7.38 (1H, d, J=15.8Hz), 4.04(3H, s), 4.00(2H, t, J=7.9Hz), 3.84 (2H, t, J=7.9Hz), 1.80–1.50 (4H, m), 0.91(3H, t, J=7.5Hz), 0.87(3H, t, J=7.4Hz)

Reference Example 1

8-Hydroxymethyl-1,3-dipropylxanthine (Compound a)

A mixture of 5,6-diamino-1,3-dipropyluracil [J. Med. Chem., 28, 487 (1985)] (10.0 g, 44.2 mmol) and glycolic acid (16.8 g, 221 mmol) was heated at 110° C. for 15 minutes. After cooling, 60 ml of dioxane and 100 ml of water were added thereto, followed by addition of sodium hydroxide to adjust the pH of the solution to 14. The resulting solution was heated under reflux for 30 minutes, cooled, and neutralized by addition of concentrated hydrochloric acid. The precipitated crystals were collected by filtration and dried to give 10.6 g (yield 90%) of Compound a as a white powder.

Melting Point: 220.1°–221.0° C.

Elemental Analysis: $C_{12}H_{18}N_4O_3$ Calcd. (%): C, 54.12; H, 6.81; N, 21.04 Found (%): C, 53.94; H, 6.97; N, 20.85

IR (KBr) $v_{max}$ (cm$^{-1}$): 3300 (br), 1703, 1632, 1556, 1510

NMR (90MHz; DMSO-d$_6$) δ (ppm): 4.50(2H, s), 4.15–3.80 (4H, m), 3.65–2.80(2H, brs), 1.90–1.45(4H, m), 1.10–0.80 (6H, m)

EI-MS: 266 (M)$^+$

Reference Example 2

8-Hydroxymethyl-7-methyl-1,3-dipropylxanthine (Compound b)

Compound a (1.00 g, 3.76 mmol) obtained in Reference Example 1 was dissolved in 30 ml of dimethylformamide. To the solution were added 1.30 g (9.40 mmol) of potassium carbonate and subsequently 0.47 ml (7.52 mmol) of methyl iodide, and the resulting mixture was stirred at 50° C. for one hour. Insoluble matters were filtered off and 60 ml of water was added to the filtrate. The mixture was extracted three times with 25 ml of chloroform. The extract was washed twice with water and twice with a saturated aqueous solution of sodium chloride, and dried over anhydrous sodium sulfate, followed by evaporation under reduced pressure. The residue was recrystallized from cyclohexane to give 735 mg (yield 70%) of Compound b as yellow needles.

Melting Point: 111.4°–111.8° C.

Elemental Analysis: $C_{13}H_{20}N_4O_3$ Calcd. (%): C, 55.70; H, 7.19; N, 19.99 Found (%): C, 55.73; H, 7.45; N, 19.64

IR (KBr) $v_{max}$ (cm$^{-1}$): 3300 (br), 1706, 1665, 1541

NMR (90MHz; CDCl$_3$) δ (ppm): 4.76(2H, s), 4.20–3.90 (4H, m), 4.02(3H, s), 2.40(1H, brs), 1.90–1.50(4H, m), 1.05–0.80(6H, m)

EI-MS: 280 (M)$^+$

Reference Example 3

7-Methyl-1,3-dipropyl-8-xanthinecarbaldehyde (Compound c)

Manganese dioxide (2.48 g, 28.5 mmol) was added to a solution of 800 mg (2.85 mmol) of Compound b obtained in Reference Example 2 in 80 ml of chloroform, and the mixture was stirred at room temperature for 12 hours. Then, the reaction mixture was filtered through Celite and the filtrate was concentrated under reduced pressure. The residue was purified by column chromatography (eluent: 1% methanol/chloroform) to give 440 mg (yield 56%) of Compound c as a pale yellow powder.

Melting Point: 129.8°–130.4° C.

IR (KBr) $v_{max}$ (cm$^{-1}$): 1716, 1694, 1664, 1591, 1543

NMR (90MHz; CDCl$_3$) δ (ppm): 9.95(1H, s), 4.33(2H, s), 4.15–3.90(4H, m), 2.00–1.50(4H, m), 1.05–0.80(6H, m)

EI-MS: 278 (M)$^+$

Reference Example 4

1,3-Diethyl-8-hydroxymethylxanthine (Compound d)

Substantially the same procedure as in Reference Example 1 was repeated using 5.0 g (25.2 mmol) of 5,6-diamino-1,3-diethyluracil [J. Am. Chem. Soc., 75, 114 (1953)] and 8.4 g (111 mmol) of glycolic acid. The resulting crude crystals were recrystallized from methanol to give 3.56 g (yield 60%) of Compound d as white needles.

NMR (270MHz; DMSO-d$_6$) δ (ppm): 13.26(1H, brs), 5.50 (1H, brs), 4.51(2H, s), 4.02(2H, q, J=6.9Hz), 3.93(2H, q, J=6.9Hz), 1.22(3H, t, J=6.9Hz), 1.12 (3H, t, J=6.9Hz)

EI-MS: 238 (M)$^+$

Reference Example 5

1,3-Diethyl-8-hydroxymethyl-7-methylxanthine (Compound e)

Substantially the same procedure as in Reference Example 2 was repeated using 2.00 g (8.40 mmol) of Compound d obtained in Reference Example 4. The resulting crude crystals were recrystallized from hexane/ethyl acetate to give 1.88 g (yield 89%) of Compound e as white needles.

NMR (270MHz; DMSO-d$_6$) δ (ppm): 5.54(1H, t, J=5.9Hz), 4.58(2H, d, J=5.9Hz), 4.01(2H, q, J=6.9Hz), 3.92 (2H, q, J=6.9Hz), 3.91(3H, s), 1.21(3H, t, J=6.9Hz), 1.12 (3H, t, J=6.9Hz)

EI-MS: 252 (M)$^+$

Reference Example 6

1,3-Diethyt-7-methyl-8-xanthinecarbaldehyde (Compound f)

Substantially the same procedure as in Reference Example 3 was repeated using 1.00 g (3.96 mmol) of Compound e obtained in Reference Example 5. The resulting crude crystals were recrystallized from hexane/ethyl acetate to give 404 mg (yield 41%) of Compound f as pale yellow plates.

NMR (270MHz; CDCl$_3$) δ (ppm): 9.93(1H, s), 4.35(3H, s), 4.20(2H, q, J=6.9Hz), 4.10(2H, q, J=6.9Hz), 1.37 (3H, t, J=6.9Hz), 1.26(3H, t, J=6.9Hz)

EI-MS: 250 (M)$^+$

Reference Example 7

(E)-8-(3-Bromostyryl)-1,3-diethylxanthine (Compound g)

3-Bromocinnamic acid (2.52 g, 11.1 mmol) and 3-(3-diethylaminopropyl)-1-ethylcarbodiimide hydrochloride (2.90 g, 15.2 mmol) were added to a solution of 5,6-diamino-1,3-diethyluracil (2.0 g, 10.1 mmol) in a dioxane (34 ml)–water (68 ml) mixture, and the resulting mixture was stirred at room temperature for 40 minutes while keeping the pH at 5.5. A 4N aqueous solution of sodium hydroxide was added thereto to adjust the pH to >14, and the mixture was heated under reflux for 20 minutes. After cooling, the mixture was neutralized and the precipitated crystals were collected by filtration. The obtained crude crystals were recrystallized from tetrahydrofuran/water to give 2.01 g (yield 37%) of Compound g as pale green plates.

Melting Point: >270° C.

Elemental Analysis: C$_{17}$H$_{17}$BrN$_4$O$_2$ Calcd. (%): C, 52.46; H, 4.40; N, 14.39 Found (%): C, 52.54; H, 4.44; N, 14.37

IR (KBr) $v_{max}$ (cm$^{-1}$): 1683, 1636, 1492

NMR (270MHz; CF$_3$COOD) δ (ppm): 7.99(1H, d, J=16.6Hz), 7.84(1H, s), 7.70(1H, d, J=7.9Hz), 7.62(1H, d, J=7.9Hz), 7.40(1H, t, J=7.9Hz), 7.19(1H, d, J=16.6Hz), 4.40–4.30(4H, m), 1.53(3H, t, J=7.2Hz), 1.41(3H, t, J=7.2Hz)

Reference Example 8

(E)-8-(3-Bromostyryl)-1,3-diethyl-7-methylxanthine (Compound h)

Compound g (2.5 g, 6.43 mmol) obtained in Reference Example 7 was dissolved in 20 ml of dimethylformamide. To the solution were added 2.22 g (16.1 mmol) of potassium carbonate and subsequently 0.8 ml (12.9 mmol) of methyl iodide, and the resulting mixture was stirred at 50° C. for 70 minutes. After cooling, insoluble matters were filtered off and water was added to the filtrate. The mixture was extracted three times with chloroform. The extract was washed three times with water and subsequently twice with a saturated aqueous solution of sodium chloride, and dried over anhydrous sodium sulfate. Evaporation under reduced pressure gave 2.37 g (yield 92%) of crude Compound h as a yellow solid, which was further recrystallized from cyctohexane/toluene to give Compound h as a yellow powder.

Melting Point: 187.3°–188.2° C.

Elemental Analysis: C$_{18}$H$_{19}$BrN$_4$O$_2$ Calcd. (%): C, 53.61; H, 4.75; N, 13.89 Found (%): C, 53.83; H, 4.63; N, 13.70

IR (KBr) $v_{max}$ (cm$^{-1}$): 1694, 1654

NMR (270MHz; DMSO-d$_6$) δ (ppm): 8.13(1H, s), 7.76 (1H, d, J=7.6Hz), 7.63(1H, d, J=15.8Hz), 7.54(1H, d, J=8.9Hz), 7.46(1H, d, J=15.8Hz), 7.37(1H, t, J=8.2Hz), 4.11–4.03 (2H, m), 4.05 (3H, s), 3.92 (2H, q, J=6.9Hz), 1.26(3H, t, J=6.9Hz), 1.13(3H, t, J=6.9Hz)

Reference Example 9

(E)-8-(3-Bromo-4-methoxystyryl)-1,3-dipropylxanthine (Compound i)

Substantially the same procedure as in Reference Example 7 was repeated using 3.0 g (13.3 mmol) of 5,6-diamino-1,3-dipropyluracil and 3.75 g (14.6 mmol) of 3-bromo-4-methoxycinnamic acid. The resulting crude crystals were recrystallized from dioxane to give 3.43 g (yield 58%) of Compound i as yellow needles.

Melting Point: 279.8°–280.6° C.

Elemental Analysis: C$_{20}$H$_{23}$BrN$_4$O$_3$ Calcd. (%): C, 53.70; H, 5.18; N, 12.52 Found (%): C, 53.77; H, 5.20; N, 12.49

IK (KBr) $v_{max}$ (cm$^{-1}$): 1685, 1633, 1599, 1503, 1279

NMR (270MHz; DMSO-d$_6$) δ (ppm): 13.42(1H, brs), 7.85 (1H, d, J=2.0Hz), 7.61(1H, dd, J=8.4, 2.0Hz), 7.55 (1H, d, J=16.3Hz), 7.15(1H, d, J=8.4Hz), 6.94(1H, d, J=16.3Hz), 3.98(2H, t, J=7.4Hz), 3.89(3H, s), 3.86(2H, t, J=7.4Hz), 1.80–1.52(4H, m), 0.89(6H, t, J=7.4Hz)

Reference Example 10

(E)-8-(3-Bromo-4-methoxystyryl)-7-methyl-1,3-dipropylxanthine (Compound j)

Substantially the same procedure as in Reference Example 8 was repeated using 750 mg (1.68 mmol) of Compound i obtained in Reference Example 9. The resulting crude crystals were recrystallized from hexane/ethyl acetate to give 588 mg (yield 76%) of Compound j as pale yellow needles.

Melting Point: 209.4°–210.8° C.

Elemental Analysis: $C_{21}H_{25}BrN_4O_3$ Calcd. (%): C, 54.67; H, 5.46; N, 12.14 Found (%): C, 54.47; H, 5.51; N, 11.91

IR (KBr) vmax(cm$^{-1}$): 1693, 1656, 1542, 1500, 1264

NMR (270MHz; CDCl$_3$) δ (ppm): 7.83(1H, d, J=2.0Hz), 7.68(1H, d, J=15.8Hz), 7.48(1H, dd, J=8.4, 2.0Hz), 6.92(1H, d, J=8.4Hz), 6.78(1H, d, J=15.8Hz), 4.13–4.07(2H, m), 4.06(3H, s), 4.01–3.97(2H, m), 3.95 (3H, s), 1.90–1.65(4H, m), 1.00(3H, t, J=7.4Hz), 0.97(3H, t, J=7.4Hz)

Reference Example 11

(E)-8-(3-Bromo-4-fluorostyryl)-1,3-diethylxanthine (Compound k)

Substantially the same procedure as in Reference Example 7 was repeated using 3.00 g (15.1 mmol) of 5,6-diamino-1,3-diethyluracil and 4.08 g (16.7 mmol) of 3-bromo-4-fluorocinnamic acid. The resulting crude crystals were recrystallized from dioxane to give 2.90 g (yield 47%) of Compound k as a pale yellow powder.

Melting Point: >300° C.

Elemental Analysis: $C_{17}H_{16}BrFN_4O_2$ Calcd. (%): C, 50.14; H, 3.96; N, 13.76 Found (%): C, 50.27; H, 3.80; N, 13.66

IR (KBr) $v_{max}$ (cm$^{-1}$): 1688, 1637, 1501, 1248

NMR (270MHz; DMSO-d$_6$) δ (ppm): 13.64 (1H, brs), 8.02 (1H, dd, J=6.9, 2.0Hz), 7.73–7.68(1H, m), 7.60 (1H, d, J=16.2Hz), 7.42(1H, t, J=8.6Hz), 7.07(1H, d, J=16.2Hz), 4.06(2H, q, J=6.9Hz), 3.94(2H, q, J=6.9Hz), 1.26 (3H, t, J=6.9Hz), 1.14 (3H, t, J=6.9Hz)

Reference Example 12

(E)-8-(3-Bromo-4-fluorostyryl)-1,3-diethyl-7-methylxanthine (Compound m)

Substantially the same procedure as in Reference Example 8 was repeated using 2.50 g (6.14 mmol) of Compound k obtained in Reference Example 11. The resulting crude crystals were recrystallized from ethyl acetate to give 2.41 g (yield 93%) of Compound m as yellow needles.

Melting Point: 217.6°–219.2° C.

Elemental Analysis: $C_{18}H_{18}BrFN_4O_2$ Calcd. (%): C, 51.32; H, 4.30; N, 13.30 Found (%): C, 51.52; H, 4.20; N, 13.34

IR (KBr) $v_{max}$ (cm$^{-1}$): 1692, 1649, 1543, 1504, 1439

NMR (270MHz; CDCl$_3$) δ (ppm): 7.80(1H, dd, J=6.6, 2.0Hz), 7.70(1H, d, J=15.8Hz), 7.52–7.46(1H, m), 7.16(1H, t, J=8.3Hz), 6.84(1H, d, J=15.8Hz), 4.21 (2H, q, J=6.9Hz), 4.09(2H, q, J=6.9Hz), 4.07(3H, s), 1.38(3H, t, J=6.9Hz), 1.26(3H, t, J=6.9Hz)

Reference Example 13

(E)-1,3-Diethyl-8-(3-methoxy-4-methoxymethoxystyryl)xanthine (Compound n)

Substantially the same procedure as in Reference Example 7 was repeated using 4.0 g (20.2 mmol) of 5,6-diamino-1,3-diethyluracil and 5.29 g (22.2 mmol) of 3-methoxy-4-methoxymethoxycinnamic acid. The resulting crude crystals were recrystallized from dioxane to give 2.93 g (yield 36%) of Compound n as pale yellow needles.

Melting Point: 223.4°–224.3° C.

Elemental Analysis: $C_{20}H_{24}N_4O_5$ Calcd. (%): C, 59.99; H, 6.04; N, 13.99 Found (%): C, 59.99; H, 6.11; N, 13.93

IR (KBr) $v_{max}$ (cm$^{-1}$): 1698, 1640, 1512, 1258

NMR (270MHz; DMSO-d$_6$) δ (ppm): 13.46(1H, brs), 7.60 (1H, d, J=16.2Hz), 7.30(1H, s), 7.10(2H, m), 6.99 (1H, d, J=16.2Hz), 5.19(2H, s), 4.06(2H, q, J=6.9Hz), 3.94(2H, q, J=6.9Hz), 3.85(3H, s), 3.40 (3H, s), 1.26(3H, t, J=6.9Hz), 1.14(3H, t, J=6.9Hz)

Reference Example 14

(E)-1,3-Diethyl-8-(3-methoxy-4-methoxymethoxystyryl)-7-methylxanthine (Compound o)

Substantially the same procedure as in Reference Example 8 was repeated using 2.0 g (5.00 mmol) of Compound n obtained in Reference Example 13. The resulting crude crystals were recrystallized from ethyl acetate to give 1.77 g (yield 85%) of Compound o as yellow plates.

Melting Point: 179.4°–180.6° C.

Elemental Analysis: $C_{21}H_{26}N_4O_5$ Calcd. (%): C, 60.86; H, 6.32; N, 13.52 Found (%): C, 61.02; H, 6.46; N, 13.43

IR (KBr) $v_{max}$ (cm$^{-1}$): 1687, 1651, 1515, 1437, 1258

NMR (270MHz; CDCl$_3$) δ (ppm): 7.74(1H, d, J=15.8Hz), 7.17(2H, m), 7.10(1H, s), 6.78(1H, d, J=15.8Hz), 5.28(2H, s), 4.22(2H, q, J=6.9Hz), 4.09(2H, q, J=6.9Hz), 4.07(3H, s), 3.96(3H, s), 3.54(3H, s), 1.39(3H, t, J=6.9Hz), 1.27(3H, t, J=6.9Hz)

Reference Example 15

(E)-1,3-Diethyl-8-(4-hydroxy-3-methoxystyryl)-7-methylxanthine (Compound p)

Compound o (1.50 g, 3.62 mmol) obtained in Reference Example 14 was suspended in tetrahydrofuran (30 ml), and 2N HCl (9 ml) was added thereto, followed by heating under reflux for one hour. The reaction mixture was neutralized with a 2N aqueous solution of sodium hydroxide under ice-cooling, and water was added thereto. The precipitated crystals were collected by filtration and recrystallized from ethyl acetate to give 1.08 g (yield 81%) of Compound p as yellow plates.

Melting Point: 185.3°–186.5° C.

Elemental Analysis: $C_{19}H_{22}N_4O_4 \cdot H_2O$ Calcd. (%): C, 58.75; H, 6.23; N, 14.42 Found (%): C, 59.13; H, 6.21; N, 14.39

IR (KBr) $v_{max}$ (cm$^{-1}$): 1687, 1657, 1650, 1515, 1276

NMR (270MHz; DMSO-d$_6$) δ (ppm): 9.45(1H, brs), 7.59(1H, d, J=15.8Hz), 7.39(1H, d, J=2.0Hz), 7.19(1H, dd, J=7.9, 2.0Hz), 7.14(1H, d, J=15.8Hz), 6.81(1H, d, J=7.9Hz), 4.06(2H, q, J=6.9Hz), 4.02(3H, s), 3.91 (2H, q, J=6.9Hz), 3.86(3H, s), 1.26(3H, t, J=6.9Hz), 1.13 (3H, t, J=6.9Hz)

Reference Example 16

(E)-1,3-Diethyl-8-(3-methoxy-4-trifluoromethanesulfonyloxystyryl)-7-methylxanthine (Compound q)

Compound p (371 mg, 1.002 mmol) obtained in Reference Example 15 was dissolved in pyridine (7 ml), and 0.34 ml (2.021 mmol) of trifluoromethanesulfonic anhydride was added thereto under ice-cooling. The resulting mixture was stirred for 2 hours under ice-cooling, and ice was added to the reaction mixture. The precipitated crystals were collected by filtration to give 523 mg (quantitative yield) of crude Compound q as a yellow solid.

Melting Point: 249.7°–251.3° C.

IR (KBr) $v_{max}$ (cm$^{-1}$): 1694, 1651, 1543, 1419, 1209

NMR (270MHz; CDCl$_3$) δ (ppm): 7.75(1H, d, J=15.8Hz), 7.27–7.18(3H, m), 6.89(1H, d, J=15.8Hz), 4.21(2H, q, J=6.9Hz), 4.09(2H, q, J=6.9Hz), 4.09(3H, s), 3.99(3H, s), 1.38(3H, t, J=6.9Hz), 1.27(3H, t, J=6.9Hz )

EI-MS: 502 (M)$^+$

Reference Example 17

(E)-1,3-Diethyl-8-(3-methoxystyryl)xanthine (Compound r)

3-Methoxycinnamic acid (2.48 g, 13.9 mmol) and 3-(3-diethylaminopropyl)-1-ethylcarbodiimide hydrochloride (3.62 g, 18.9 mmol) were added to a mixture of dioxane (80 ml) and water (40 ml) containing 5,6-diamino-1,3-diethyluracil [J. Am. Chem. Soc., 75, 114 (1953)] (2.5 g, 12.6 mmol). The resulting solution was stirred at room temperature for 2 hours at pH 5.5. After a 4N aqueous solution of sodium hydroxide was added thereto to adjust the pH to >14, 40 ml of water was added and the mixture was heated under reflux for 20 minutes. After cooling, the mixture was neutralized and 50 ml of chloroform was added thereto. The organic layer was separated and the aqueous layer was extracted twice with 50 ml of chloroform. The combined extract was washed with a saturated aqueous solution of sodium chloride and dried over anhydrous sodium sulfate, followed by evaporation under reduced pressure. The residue was recrystallized from dimethylformamide/water to give 2.10 g (yield 49%) of Compound r as a white powder.

Melting Point: 270.6°–272.5° C.

Elemental Analysis: C$_{18}$H$_{20}$N$_4$O$_3$ Calcd. (%): C, 63.52; H, 5.92; N, 16.46 Found (%): C, 63.20; H, 6.01; N, 16.34

IR (KBr) $v_{max}$ (cm$^{-1}$): 1686, 1634, 1500

NMR (270MHz; DMSO-d$_6$) δ (ppm): 7.61(1H, d, J=16.4Hz), 7.34(1H, t, J=7.9Hz), 7.20–7.18(2H, m), 7.07 (1H, d, J=16.4Hz), 6.92(1H, d, J=8.6Hz), 4.06(2H, q, J=7.0Hz), 3.94(2H, q, J=6.8Hz), 3.81(3H, s), 1.26 (3H, t, J=7.0Hz), 1.14(3H, t, J=6.8Hz)

Reference Example 18

(E)-1,3-Diethyl-8-(3-methoxystyryl)-7-methylxanthine (Compound s)

Compound r (1.70 g, 5.0 mmol) obtained in Reference Example 17 was dissolved in 40 ml of dimethylformamide. To the solution were added 1.73 g (12.5 mmol) of potassium carbonate and subsequently 0.62 ml (10.0 mmol) of methyl iodide, and the resulting mixture was stirred at 50° C. for 30 minutes. After cooling, insoluble matters were filtered off, and 100 ml of water was added to the filtrate. The mixture was extracted three times with 50 ml of chloroform. The extract was washed twice with water and once with a saturated aqueous solution of sodium chloride, and dried over anhydrous sodium sulfate, followed by evaporation under reduced pressure. The obtained crude crystals were purified by silica gel column chromatography (eluent: 40% ethyl acetate/hexane), followed by recrystallization from cyclohexane/toluene to give 1.10 g (yield 62%) of Compound s as pale yellow needles.

Melting Point: 153.4°–154.8° C.

Elemental Analysis: C$_{19}$H$_{22}$N$_4$O$_3$ Calcd. (%): C, 64.39; H, 6.26; N, 15.81 Found (%): C, 64.34; H, 6.38; N, 15.82

IR (KBr) $v_{max}$ (cm$^{-1}$): 1692, 1656, 1541

NMR (270MHz; DMSO-d$_6$) δ (ppm): 7.64(1H, d, J=15.8Hz), 7.40–7.30(4H, m), 6.97–6.92(1H, m), 4.31–4.05 (2H, m), 4.05 (3H, s), 3.92 (2H, q, J=7.0Hz), 3.82 (3H, s), 1.26(3H, t, J=7.1Hz), 1.13(3H, t, J=7.0Hz)

Preparation Example 1

Tablets

Tablets having the following composition were prepared in a conventional manner.

| Composition of One Tablet | |
|---|---|
| Compound 24 | 20 mg |
| Lactose | 143.4 mg |
| Potato Starch | 30 mg |
| Hydroxypropylcellulose | 6 mg |
| Magnesium Stearate | 0.6 mg |
| | 200 mg |

Preparation Example 2

Fine Granules

Fine granules having the following composition were prepared in a conventional manner.

| Composition of One Pack of Fine Granules | |
|---|---|
| Compound 28 | 20 mg |
| Lactose | 655 mg |
| Corn Starch | 285 mg |
| Hydroxypropylcellulose | 40 mg |
| | 1,000 mg |

Preparation Example 3

Capsules

Capsules having the following composition were prepared in a conventional manner.

| Composition of One Capsule | |
|---|---|
| Compound 30 | 20 mg |
| Avicel | 99.5 mg |
| Magnesium Stearate | 0.5 mg |
| | 120 mg |

Preparation Example 4

Injections

Injections having the following composition were prepared in a conventional manner.

| Composition of One Injection Vial | |
|---|---|
| Compound 1 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Preparation Example 5

Syrup Preparations

Syrup Preparations having the following composition were prepared in a conventional manner.

| Composition of One Syrup Preparation | |
|---|---|
| Compound 21 | 20 mg |
| Refined Sugar | 30 mg |
| Ethyl p-Hydroxybenzoate | 40 mg |
| Propyl p-Hydroxybenzoate | 10 mg |
| Strawberry Flavor | 0.1 ml |
| Water | 99.8 ml |
| | 100 ml |

What is claimed is:

1. A xanthine derivative represented by the following Formula (I):

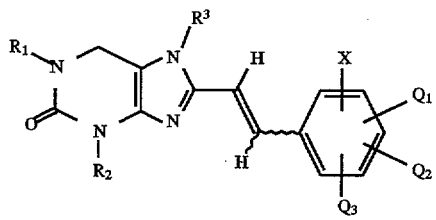 (I)

in which $R^1$, $R^2$, and $R^3$ independently represent hydrogen or lower alkyl;

$Q^1$, $Q^2$, and $Q^3$ independently represent hydrogen, lower alkyl, lower alkoxy, or halogen;

and X represents —$COR^4$ (in which $R^4$ represents hydrogen, hydroxy, lower alkyl, or lower alkoxy) or —$SO_2R^5$ {in which $R^5$ represents hydroxy, lower alkoxy, trifluoromethyl,

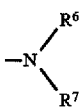

in which $R^6$ and $R^7$ independently represent hydrogen, hydroxy-substituted or unsubstituted lower alkyl, aryl, or

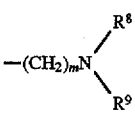

(in which m represents an integer of 1 to 3; and $R^8$ and $R^9$ independently represent hydrogen or lower alkyl), or

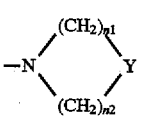

(in which Y represents a single bond, oxygen, or N—$R^{10}$ in which $R^{10}$ represents hydrogen or lower alkyl; and n1 and n2 independently represent an integer of 1 to 3)}, or a pharmaceutically acceptable salt thereof.

2. A xanthine derivative according to claim 1, in which $R^1$, $R^2$, and $R^3$ are independently lower alkyl.

3. A xanthine derivative according to claim 2, in which $R^3$ is methyl.

4. A xanthine derivative according to claim 3, in which $R^1$ and $R^2$ are independently ethyl or propyl.

5. A xanthine derivative according to claim 4, in which the configuration at the position 8 of the xanthine ring is (E) form.

6. A xanthine derivative according to claim 5, in which X is —$COR^4$.

7. A xanthine derivative according to claim 6, in which X is acetyl.

8. A xanthine derivative according to claim 7, in which said derivative is (E)-8-(3-acetylstyryl)-1,3-diethyl-7-methyl-xanthine, (E)-8-(3-acetyl-4-fluorostyryl)-1,3-diethyl-7-methylxanthine, or (E)-8-(4-acetyl-3-methoxystyryl)-1,3-diethyl-7-methylxanthine.

9. A xanthine derivative according to claim 5, in which X is —$SO_2R^5$.

10. A therapeutic pharmaceutical composition comprising a pharmaceutical carrier and the compound defined by any of claims 1 to 9.

* * * * *

UNITED STATES PATENT AND TRADEMARK OFFICE
CERTIFICATE OF CORRECTION

PATENT NO. : 5,670,498
DATED : September 23, 1997
INVENTOR(S) : FUMIO SUZUKI ET AL.

Page 1 of 4

It is certified that error appears in the above-identified patent and that said Letters Patent is hereby corrected as shown below:

ON TITLE PAGE AT [56], REFERENCES CITED
  Under U.S. PATENT DOCUMENTS insert:
    --3,641,010   2/1972   Schwiss et al. ........ 260/240--.

Under FOREIGN PATENTS DOCUMENTS insert:
    --W006976   4/1992   PCT--.

Under OTHER PUBLICATIONS, after "Abstract for Larsen",
    "Narske Laege Foren" should read --Norske Laegeforen--.

ON TITLE PAGE AT [57], ABSTRACT

After "Formula (I):"

"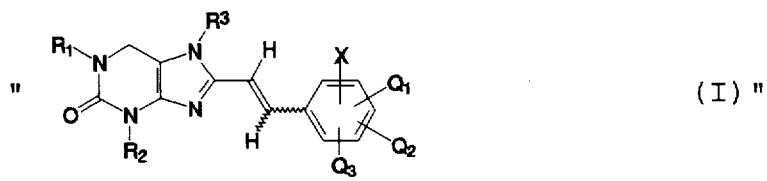 (I)"

should read

--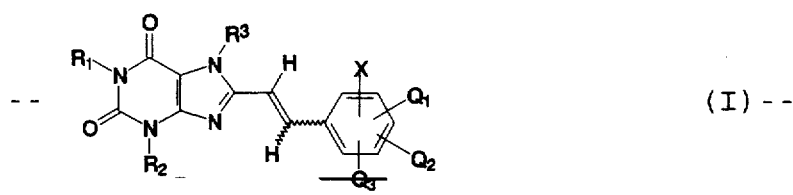 (I)--

UNITED STATES PATENT AND TRADEMARK OFFICE
CERTIFICATE OF CORRECTION

PATENT NO. : 5,670,498
DATED : September 23, 1997
INVENTOR(S) : FUMIO SUZUKI ET AL.

It is certified that error appears in the above-identified patent and that said Letters Patent is hereby corrected as shown below:

COLUMN 2
Line 13:

"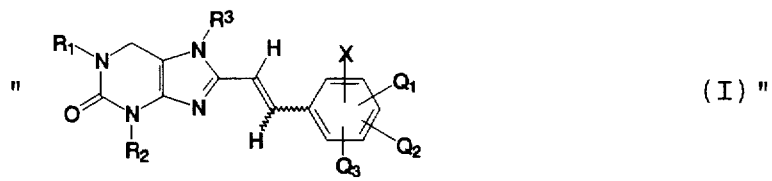 (I)"

should read

--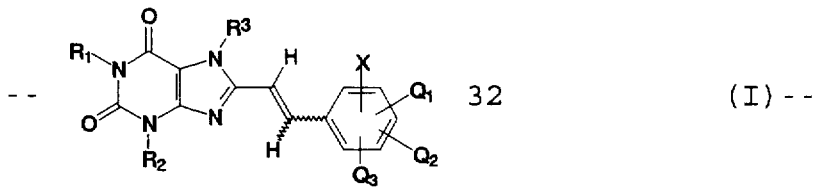 32 (I)--

COLUMN 3
Line 15, "aluminium" should read --aluminum--.

COLUMN 5
Line 14, "$\underset{R2}{|}$" should read --$\overset{|}{R^2}$--.

(IV)

UNITED STATES PATENT AND TRADEMARK OFFICE
CERTIFICATE OF CORRECTION

PATENT NO. : 5,670,498
DATED : September 23, 1997
INVENTOR(S) : FUMIO SUZUKI ET AL.

It is certified that error appears in the above-identified patent and that said Letters Patent is hereby corrected as shown below:

COLUMN 15
 Line 49, "[]$^3$H-CGS 21689" shuld read --$^3$H-CGS 21680--;
 Line 63, "at2which" should reat --at which--.

COLUMN 29
 Line 43, "32%" should read --32%)--.

COLUMN 31
 Line 48, "Diethyt" should read --Diethyl--.

COLUMN 32
 Line 39, "cyctohexane/toluene" should read
  --cyclohexane/toluene"--.

UNITED STATES PATENT AND TRADEMARK OFFICE
CERTIFICATE OF CORRECTION

PATENT NO. : 5,670,498
DATED : September 23, 1997
INVENTOR(S) : FUMIO SUZUKI ET AL.

It is certified that error appears in the above-identified patent and that said Letters Patent is hereby corrected as shown below:

COLUMN 37
Line 35,

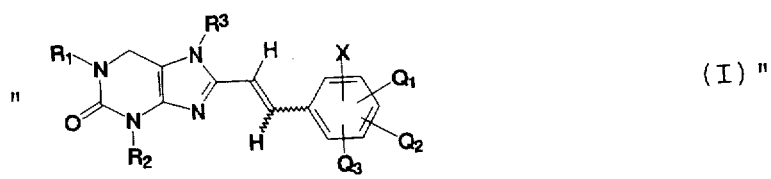 (I) "

should read

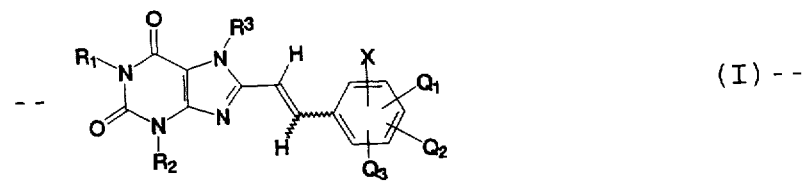 (I) --

Signed and Sealed this

Twenty-sixth Day of May, 1998

Attest:

BRUCE LEHMAN

Attesting Officer    Commissioner of Patents and Trademarks